(12) United States Patent
Shen

(10) Patent No.: US 10,672,937 B2
(45) Date of Patent: Jun. 2, 2020

(54) OPTICAL SENSOR MODULE AND SENSOR CHIP THEREOF

(71) Applicant: PIXART IMAGING INC., Hsin-Chu (TW)

(72) Inventor: Chi-Chih Shen, Hsin-Chu (TW)

(73) Assignee: PIXART IMAGING INC., Hsin-Chu (TW)

( * ) Notice: Subject to any disclaimer, the term of this patent is extended or adjusted under 35 U.S.C. 154(b) by 0 days.

(21) Appl. No.: 15/646,533

(22) Filed: Jul. 11, 2017

(65) Prior Publication Data

US 2017/0309771 A1    Oct. 26, 2017

Related U.S. Application Data

(63) Continuation-in-part of application No. 15/096,601, filed on Apr. 12, 2016, now Pat. No. 9,741,875.

(30) Foreign Application Priority Data

Sep. 2, 2015    (TW) .............................. 104128990 A

(51) Int. Cl.
*H01L 31/147*    (2006.01)
*H01L 31/0216*    (2014.01)
(Continued)

(52) U.S. Cl.
CPC ........ *H01L 31/147* (2013.01); *H01L 23/3185* (2013.01); *H01L 31/0203* (2013.01); *H01L 31/02005* (2013.01); *H01L 31/02164* (2013.01); *H01L 31/143* (2013.01); *H01L 31/1876* (2013.01); *A61B 5/024* (2013.01); *A61B 5/14551* (2013.01); *G06K 9/00013* (2013.01); *G06K 9/00087* (2013.01); *H01L 24/13* (2013.01); *H01L 24/16* (2013.01); *H01L 24/48* (2013.01); *H01L 2224/13009* (2013.01); *H01L 2224/16225* (2013.01); *H01L 2224/48091* (2013.01); *H01L 2224/49171* (2013.01); *H01L 2924/00014* (2013.01);
(Continued)

(58) Field of Classification Search
None
See application file for complete search history.

(56) References Cited

U.S. PATENT DOCUMENTS 9,402,316 B2    7/2016    Arnold et al.
9,812,521 B2 *    11/2017    Hsiao .................. H01L 28/10
(Continued)

FOREIGN PATENT DOCUMENTS

CN    202994184 U    6/2013
CN    104051366 A    9/2014
(Continued)

*Primary Examiner* — Telly D Green
(74) *Attorney, Agent, or Firm* — Li & Cai Intellectual Property (USA) Office

(57) ABSTRACT

An optical sensor module and a sensor chip thereof are provided. The optical sensor module includes a substrate, a sensor chip and a passive chip. The sensor chip is disposed on the substrate, and the sensor chip includes a chip body having an active region located at a top side thereof and a recess portion depressed from a top surface of the chip body. The passive chip is accommodated in the recess portion, and a depth of the recess portion is greater than a thickness of the passive chip.

19 Claims, 17 Drawing Sheets

(51) Int. Cl.
*H01L 31/02* (2006.01)
*H01L 31/0203* (2014.01)
*H01L 31/18* (2006.01)
*H01L 31/14* (2006.01)
*H01L 23/31* (2006.01)
*G06K 9/00* (2006.01)
*A61B 5/024* (2006.01)
*A61B 5/1455* (2006.01)
*H01L 23/00* (2006.01)

(52) U.S. Cl.
CPC ........... *H01L 2924/10155* (2013.01); *H01L 2924/10253* (2013.01); *H01L 2924/19104* (2013.01)

(56) References Cited

U.S. PATENT DOCUMENTS

| | | | |
|---|---|---|---|
| 2006/0043514 A1* | 3/2006 | Shizuno | H01L 24/10 257/434 |
| 2006/0197187 A1* | 9/2006 | Lohninger | H01L 21/6835 257/584 |
| 2009/0298220 A1* | 12/2009 | Anderson | H01L 27/14636 438/70 |
| 2012/0305771 A1* | 12/2012 | Lai | G01S 7/4813 250/338.4 |
| 2013/0075764 A1* | 3/2013 | Yu | H01L 25/167 257/82 |
| 2013/0292786 A1* | 11/2013 | Sengupta | H01L 31/0203 257/432 |
| 2013/0307125 A1 | 11/2013 | Huang et al. | |
| 2014/0332969 A1 | 11/2014 | Ho et al. | |
| 2015/0228557 A1 | 8/2015 | Cheng et al. | |
| 2016/0141440 A1* | 5/2016 | Chun | H01L 31/12 257/82 |
| 2016/0380041 A1* | 12/2016 | Hsiao | H01L 28/10 257/531 |
| 2017/0140195 A1 | 5/2017 | Wang et al. | |
| 2018/0026090 A1* | 1/2018 | Hsiao | H01L 28/10 257/531 |
| 2018/0108585 A1 | 4/2018 | Wang et al. | |

FOREIGN PATENT DOCUMENTS

| | | |
|---|---|---|
| CN | 104347560 A | 2/2015 |
| CN | 104835793 A | 8/2015 |
| CN | 104851853 A | 8/2015 |

* cited by examiner

OPTICAL SENSOR MODULE AND SENSOR CHIP THEREOF

CROSS REFERENCE TO RELATED APPLICATION

This application is a continuation-in-part of U.S. application Ser. No. 15/096,601, filed on Apr. 12, 2016 and entitled "SENSOR CHIP PACKAGE STRUCTURE AND MANUFACTURING METHOD THEREOF", the entire disclosures of which are incorporated herein by reference.

BACKGROUND OF THE INVENTION

1. Field of the Invention

The instant disclosure relates to a sensor chip package structure and the manufacturing method thereof; in particular, to a sensor chip package structure having an exposed active region and the manufacturing method thereof.

2. Description of Related Art

Currently optical sensor package module includes a substrate, a chip, and a molding compound. The chip is disposed on the substrate and electrically connected thereto, and the molding compound encapsulates the substrate and the chip to fix and protect the chip and the wires. In addition, the sensing region of the chip is usually covered by glass or other transparent material so that the sensing region is not exposed. However, when the optical sensor package module is implemented in a fingerprint identification device, the identification accuracy may be impacted because the finger cannot directly touch the sensing region.

Furthermore, the sensing region is covered by the transparent material which would increase the thickness of the optical sensor package module, which may not benefit the integration of the optical sensor package module with the portable electronic device.

SUMMARY OF THE INVENTION

The object of the instant disclosure is to provide a sensor chip package structure. In the sensor chip package structure, the active region of the sensor chip is exposed without being covered by any glass or the other transparent material so that the sensor chip package structure can be implemented in many kinds of sensing devices. Furthermore, by forming a concave portion on the sensor chip, the distance between the source and the active region can be shortened.

In order to achieve the aforementioned objects, according to an embodiment of the instant disclosure, an optical sensor module is provided. The optical sensor module includes a substrate, a sensor chip, and a passive chip. The sensor chip is disposed on the substrate, and the sensor chip includes a chip body having an active region located at a top side thereof and a recess portion depressed from a top surface thereof. The passive chip is accommodated in the recess portion, and the recess portion has a depth greater than a thickness of the passive chip.

According to another embodiment of the instant disclosure, a sensor chip is provided. The sensor chip includes a chip body having an active region located at a top side thereof and a recess portion depressed from a top surface thereof for accommodating a passive chip, wherein the recess portion has a depth greater than a thickness of the passive chip.

To sum up, the optical sensor module and the sensor chip in accordance with the instant disclosure can make the active region be exposed to the external environment to be touched by an object, such as a finger. In addition, the chip body of the sensor chip includes at least one recess portion depressed from the top surface thereof so that the passive chip can be accommodated in the recess portion, thereby shortening the distance between the passive chip and the active region.

In order to further the understanding regarding the instant disclosure, the following embodiments are provided along with illustrations to facilitate the disclosure of the instant disclosure.

DETAILED DESCRIPTION OF THE PREFERRED EMBODIMENTS

Figure 1A:
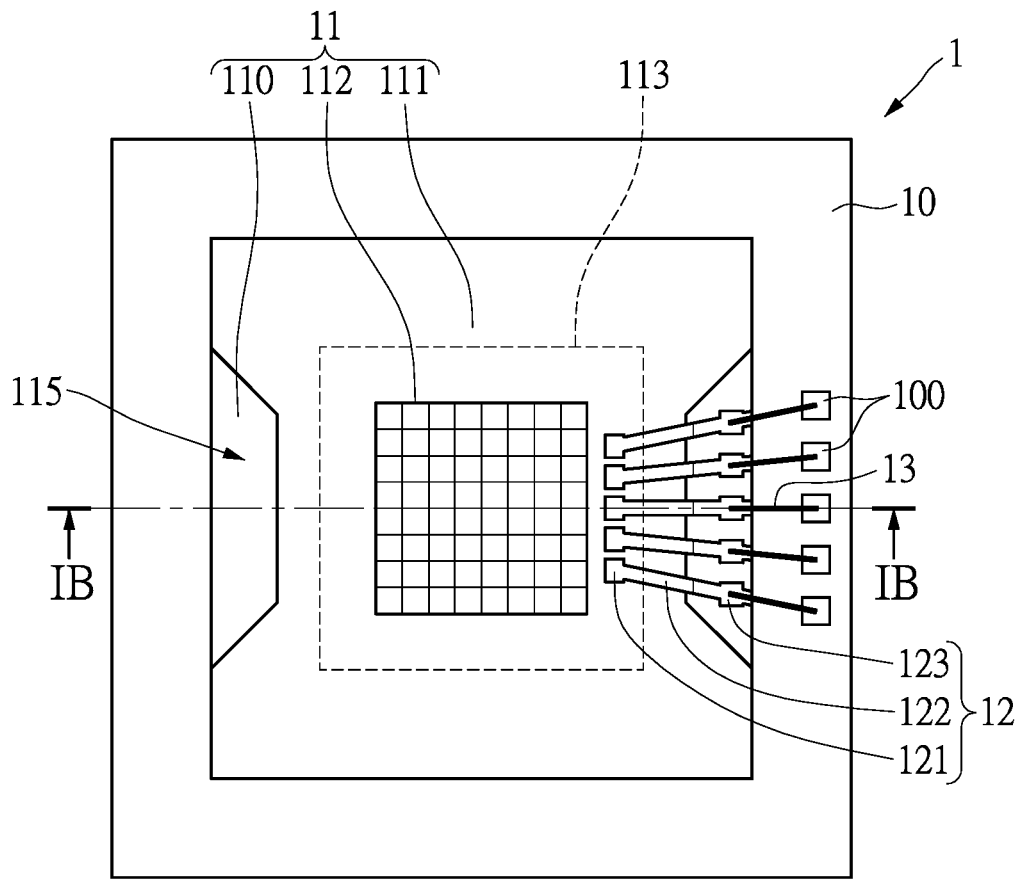
FIG. 1A shows a top view of a sensor chip package structure in accordance with an embodiment of the instant disclosure.

The aforementioned illustrations and following detailed descriptions are exemplary for the purpose of further explaining the scope of the instant disclosure. Other objectives and advantages related to the instant disclosure will be illustrated in the subsequent descriptions and appended drawings. In reference to the disclosure herein, for purposes of convenience and clarity only, directional terms, such as, top, bottom, left, right, up, down, over, above, below, beneath, rear, front, distal, and proximal are used with respect to the accompanying drawings. Such directional terms should not be construed to limit the scope of the invention in any manner. In addition, the same reference numerals are given to the same or similar components.

Figure 1B:
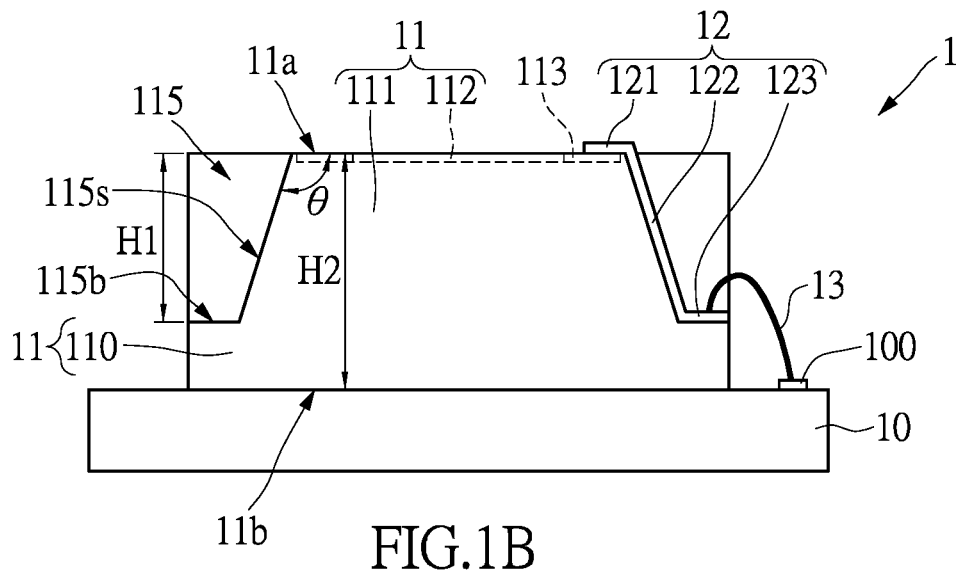
FIG. 1B shows a sectional view taken along line IB-IB of FIG. 1A.

Please refer to FIG. 1A and FIG. 1B. FIG. 1A shows a top view of a sensor chip package structure in accordance with an embodiment of the instant disclosure, and FIG. 1B shows a sectional view taken along line of FIG. 1A.

The sensor chip package structure provided in the embodiment of the instant disclosure can be implemented in different sensing devices, such as a fingerprint identification device, a sweat duct identification device, an oximeter detector, a heartbeat sensor, an ambient light sensor, or a proximity sensor. In the embodiment of the instant disclosure, the sensor chip package structure 1 includes a substrate 10, a sensor chip 11, and a wiring layer 12.

The substrate 10 can be a metal plate, an insulating plate, or a composite plate, in which the composite plate may be a printed circuit board (PCB) or a flexible printed circuit (FPC). In the instant embodiment, the substrate 10 is a printed circuit board, the substrate 10 has a plurality of traces (not shown in FIG. 1) embedded therein and a plurality of pads 100 disposed thereon, in which the pads 100 can be arranged according to the position of the sensor chip 11.

Additionally, in the embodiment shown in FIG. 1A, the top view of the substrate 10 has a basic rectangular shape, but the shape of the substrate 10 is not limited to the example provided herein. In another embodiment, the substrate 10 may have another geometric shape, such as circular shape, elliptical shape, square shape, or triangular shape.

The sensor chip 11 is mounted on the substrate 10 and electrically connected to one of the pads 100 disposed on the substrate 10 through at least one bonding wire 13. Specifically, the sensor chip 11 has a top surface 11a and a lower surface 11b opposite to the top surface 11a. The sensor chip 11 includes an active region 112 and a wiring region 113 surrounding the active region 112, in which the active region and the wiring region are defined on the top surface 11a. A control circuit, which is electrically connected to the active region 112, has been laid out in the wiring region 113 to receive the signal detected by the active region 112.

Notably, the sensor chip 11 has at least one concave portion 115 depressed from the top surface 11a, and the concave portion 115 is located at one side of the active region 112 and extends transversely through a side surface of the sensor chip 11.

Please refer to FIG. 1B. The concave portion 115 has a sidewall surface 115s and a bottom surface 115b. The sidewall surface 115s is connected between the top surface 11a and the bottom surface 115b. In one embodiment, the sidewall surface 115s is an inclined surface, which is inclined relative to the bottom surface 115b. Specifically, the sidewall surface 115s and the top surface 11a form an angle θ ranging from 110 to 140 degree. In addition, a depth H1 of the concave portion 115 is less than a height H2 of the sensor chip 11. The height H2 of the sensor chip 11 means the perpendicular distance between the top surface 11a and the lower surface 11b. Furthermore, the depth H1 of the concave portion 115 ranges from 100 to 400 μm.

That is to say, the sensor chip 11 includes a base portion 110 and a protruding portion 111 protruding from an upper surface of the base portion 110. The previously mentioned concave portion 115 is defined by the protruding portion 111 and the base portion 110. Accordingly, the area of a top-view figuration of the protruding portion 111 is smaller than that of the base portion 110, and the upper surface of the base portion 110 is the bottom surface 115b of the concave portion 115.

In the embodiment shown in FIGS. 1A and 1B, the sensor chip 11 includes two concave portions 115, which are respectively located at two opposite sides of the active region 112. However, the number and the location of the concave portion 115 can be determined according to the wiring layout design, and are not limited to the example provided herein. For example, two concave portions 115 can be located at two adjacent sides of the active region 112. In another embodiment, the sensor chip 11 can have only one or more than two concave portions 115.

Please refer to FIG. 1A and FIG. 1B. The wiring layer 12 is disposed on the sensor chip 11 and electrically connected to the active region 112. Specifically, the wiring layer 12 is laid on the top surface 11a of the sensor chip 11, the sidewall surface 115s and the bottom surface 115b of the concave portion 115. Furthermore, the wiring layer 12 is electrically connected to the active region 112 through the control circuit arranged in the wiring region 113.

In one embodiment, the wiring layer 12 includes at least one first contact pad 121, at least one second contact pad 123 and a wire 122 connected between the first and second contact pads 121, 123. The number of the first and second contact pads 121, 123 and wire 122 can be adjusted according to practical demands of the sensor chips and is not intended to limit the instant disclosure.

It is worth noting that the first contact pad 121 is disposed on the top surface 11a of the sensor chip 11 and electrically connected to the control circuit arranged in the wiring region 113. The second contact pad 123 is disposed on the bottom surface 115b of the concave portion 115, and at least a portion of the wire 122 extends from the first contact pad 121 disposed on the top surface 11a along the sidewall surface 115s to connect to the second contact pad 123. The second contact pad 123 is electrically connected to the pad 100 through the bonding wire 13. As such, the active region 112 of the sensor chip 11 can be electrically connected to the traces embedded in the substrate 10.

That is, the sidewall surface 115s and the bottom surface 115b of the concave portion 115 can serve as a layout region, so that the active region 112 can be electrically connected to the substrate 10 through the wiring layer 12 disposed on the sidewall surface 115s and the bottom surface 115b of the concave portion 115 and the bonding wire 13.

Figure 2:
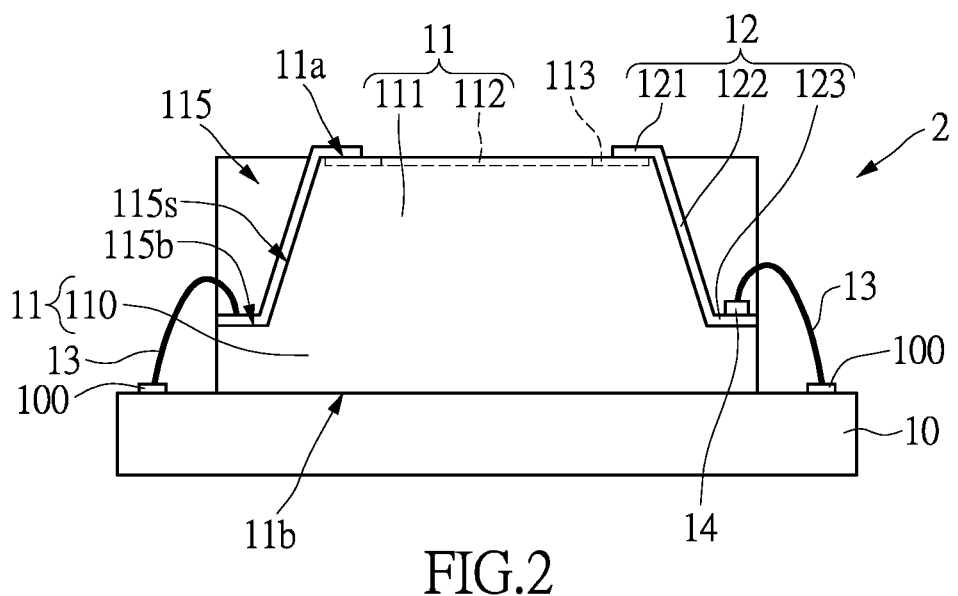
FIG. 2 shows a sectional view of the sensor chip package structure in accordance with another embodiment of the instant disclosure.

Please refer to FIG. 2. FIG. 2 shows a sectional view of the sensor chip package structure in accordance with another embodiment of the instant disclosure. The same reference numerals are given to the same components or to components corresponding to those in FIG. 1B, and descriptions of the common portions are omitted.

In the instant embodiment, the sensor chip package structure 2 further includes a light-emitting element 14 accommodated in the concave portion 115. Specifically, the light-emitting element 14 is disposed on the bottom surface 115b of the concave portion 115. The light-emitting element 14 has a thickness less than the depth of the concave portion 115.

The light-emitting element 14 is used to project a light beam on an object to be tested. Thereafter, the active region 112 of the sensor chip 11 receives the reflected light beam reflected off the object to form an image of the object and for identification. The light-emitting element 14 can be an LED, a laser source, or an infrared light source to provide a monochromatic light or a polychromatic light.

In the instant embodiment, the light-emitting element 14 is an LED, and the ground terminal and voltage input terminal of the LED are respectively located at a bottom portion and a top portion of the LED. Accordingly, when the light-emitting element 14 is arranged in the concave portion 115, the light-emitting element 14 can be disposed on one of the second contact pad 123 which is grounded, so that the ground terminal located at the bottom portion of the light-emitting element 14 can be directly grounded.

In addition, in the instant embodiment, the substrate 10 includes a switching control circuit, and the voltage input terminal located at the top portion of the light-emitting element 14 can be electrically connected to the switching control circuit through the pad 100 and one of the bonding wires 13 connecting to the pad 100. As such, the switching control circuit can control the turn on and turn off of the light-emitting element 14.

In another embodiment, both of the ground terminal and the voltage input terminal are disposed on a top portion of the light-emitting element 14. In this case, the light-emitting element 14 does not have to be disposed on the second contact pad 123. That is, the light-emitting element 14 can be disposed on a region of the bottom surface 115b of the concave portion 115 and not covered by the wiring layer 12. Furthermore, the ground terminal and the voltage input terminal of the light-emitting element 14 can be respectively electrically connected to two different pads 100 respectively through two bonding wires 13, in which one of the pads 100 is grounded, and the other one is electrically connected to the switching control circuit.

It is worth noting that in the prior art sensor chip package, both the light source and the chip are directly mounted on the substrate, and the distance between the light source and the sensing region of the chip cannot be further shortened because of the structural limitation of the chip.

In the instant embodiment, the light-emitting element 14 can be directly formed on the sensor chip 11 by forming the concave portion 115 on the top surface 11a of the sensor chip 11. As such, the horizontal distance between the light-emitting element 14 and the active region 112 can be shortened so as to increase the image identification accuracy. In addition, compared to the prior art sensor chip package, the whole size of the sensor chip package structures provided by the instant disclosure can be further minimized.

In one embodiment, the sensor chip package structure 2 can include at least two light-emitting elements 14 for emitting two light beams of different colors and can be implemented in the oximeter detector. Under these circumstances, the sensor chip 11 can have at least two concave portions 115 to respectively accommodate these light-emitting elements 14. That is, compared to the prior art sensor chip package, the whole size of the sensor chip package structure 2 can be maintained at a predetermined level, instead of being increased significantly with the increasing number of the light-emitting elements 14.

Figure 3A:
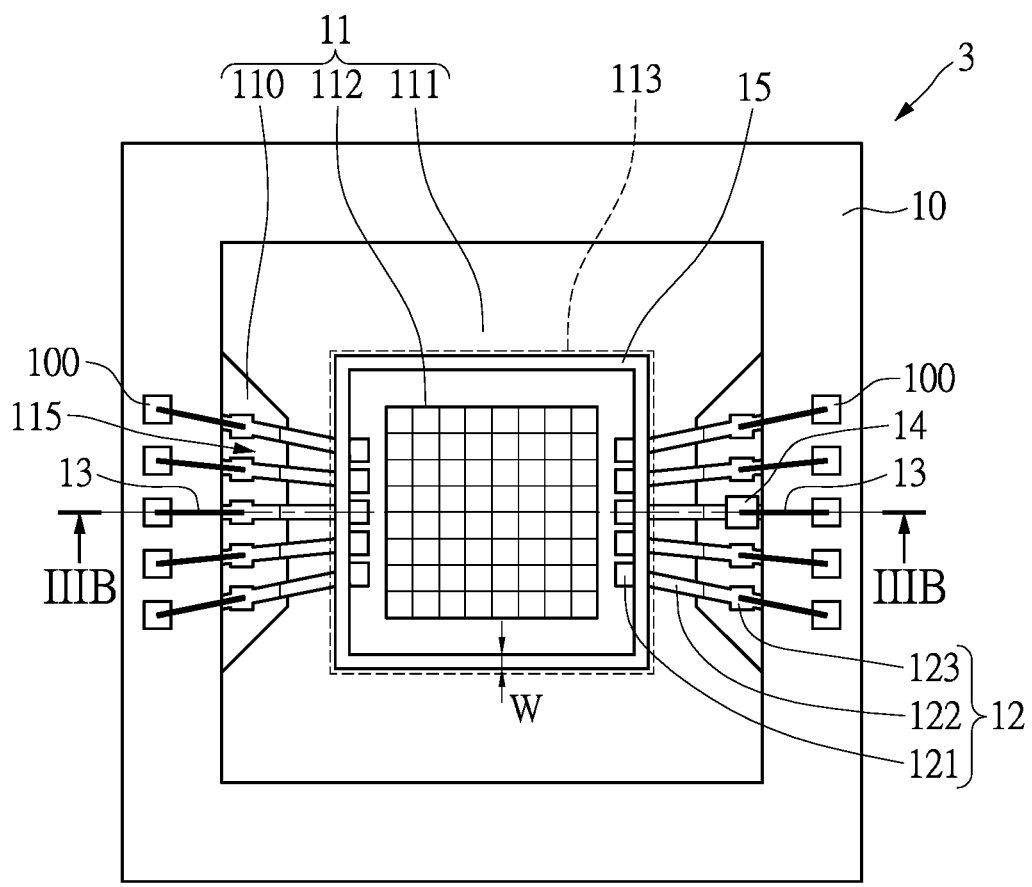
FIG. 3A shows a top view of a sensor chip package structure in accordance with another embodiment of the instant disclosure.
Figure 3B:
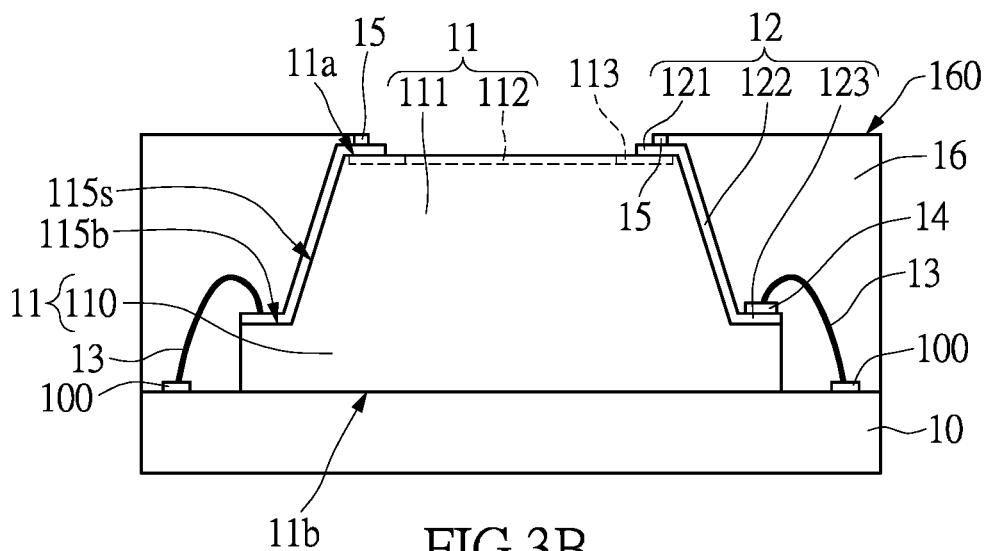
FIG. 3B shows a sectional view taken along line IIIB-IIIB of FIG. 3A.

Subsequently, please refer to FIG. 3A and FIG. 3B. FIG. 3A shows a top view of a sensor chip package structure in accordance with another embodiment of the instant disclosure, and FIG. 3B shows a sectional view taken along line IIIB-IIIB of FIG. 3A. In the sensor chip package structure 3 of this embodiment, elements similar to those shown in FIG. 2 are denoted by similar reference numerals, and redundant description is omitted.

In the instant embodiment, the sensor chip package structure 3 of the instant embodiment further includes a dam 15 and a molding compound 16.

Please refer to FIG. 3A. The dam 15 is disposed on the top surface 11a of the sensor chip 11 and surrounds the active region 112 to define an enclosed opening, which can prevent the active region 112 from being covered by the molding compound 16 during the formation of the molding compound 16. The functions of the dam 15 will be explained together with the manufacturing method of the sensor chip package structure in the following description and are omitted herein.

In addition, in the instant embodiment, the dam 15 and a portion of the wiring layer 12 disposed on the top surface 11a of the sensor chip 11 partially overlap with each other in a thickness direction of the sensor chip 11. As shown in FIG. 3B, the dam 15 is stacked on the wiring layer 12 (the first contact pad 121) to protect the wiring layer 12 from oxidation or damage. In one embodiment, the dam 15 has a height ranging from 2 to 50 μm, and a width (W) ranging from 5 to 100 μm.

However, as long as the dam 15 can prevent the molding compound 16 from covering the active region 112, the relative positions between the dam 15 and the wiring layer 12 are not limited. In another embodiment, a portion of the wiring layer 12 can be stacked on the dam 15, or the dam 15 is directly disposed on the top surface 11a of the sensor chip 11 without overlapping with the wiring layer 12. Furthermore, the dam 15 can be made of photo-imageable material, such as photoresist material for use in lithography process or the other insulating material.

The molding compound 16 covers the substrate 10, a portion of the sensor chip 11, and the wiring layer 12. Notably, the molding compound 16 has a top face 160 that is coplanar with or lower than an end face of the dam 15. That is, the active region 112 of the sensor chip 11 would be exposed to the external environment through the enclosed opening defined by the dam 15 rather than covered by the molding compound 16, to sensor an object to be tested.

In the instant embodiment, the molding compound 16 can be made of a material transparent to the light beam emitted by the light-emitting element 14, so that the light beam can be projected on the object to be tested. For example, when the light beam is visible light, the molding compound 16 can be made of a material transparent to the visible light. In another embodiment, when the light beam is infrared light, the molding compound 16 can be made of a material transparent to the infrared light.

It is worth noting that the sensor chip package structure 1 shown in FIGS. 1A and 1B also can include the dam 15 and the molding compound 16. When the sensor chip package structure 1 does not include the light-emitting element 14, the material for forming the molding compound 16 can be selected from opaque or transparent materials and is not limited to the transparent material.

In an embodiment of the instant disclosure, a manufacturing method of the sensor chip package structure is provided. Please refer to FIG. 4, which shows a flowchart of a manufacturing method of the sensor chip package structure in accordance with another embodiment of the instant disclosure.

In step S100, a wafer is provided. The wafer includes a plurality of sensor chips, and each sensor chip includes an active region and defines a pre-thinned region thereon. The pre-thinned region is positioned at one side of the active region and covers a boundary line of the sensor chip.

Figure 4:
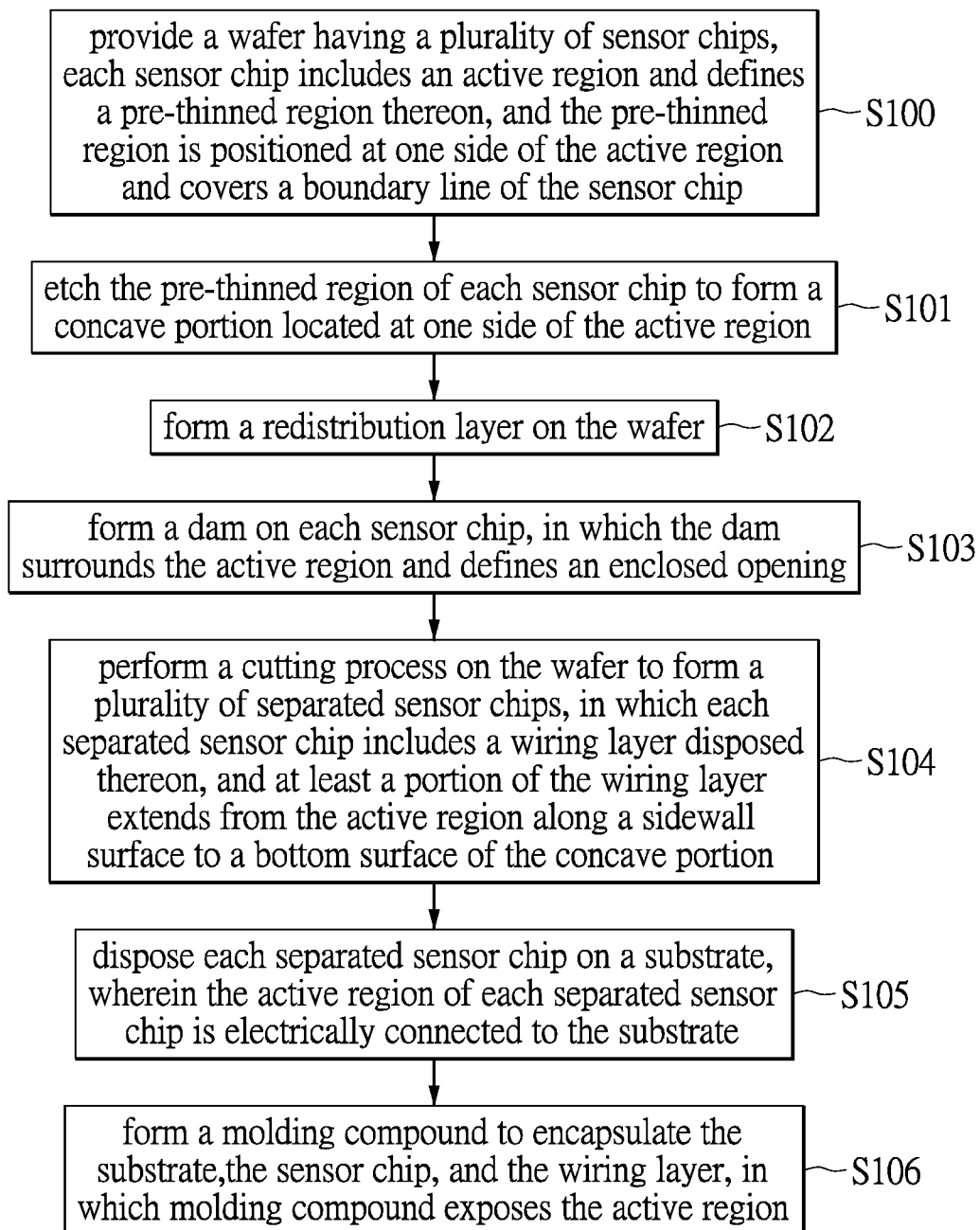
FIG. 4 shows a flowchart of a manufacturing method of the sensor chip package structure in accordance with another embodiment of the instant disclosure.
Figure 5:
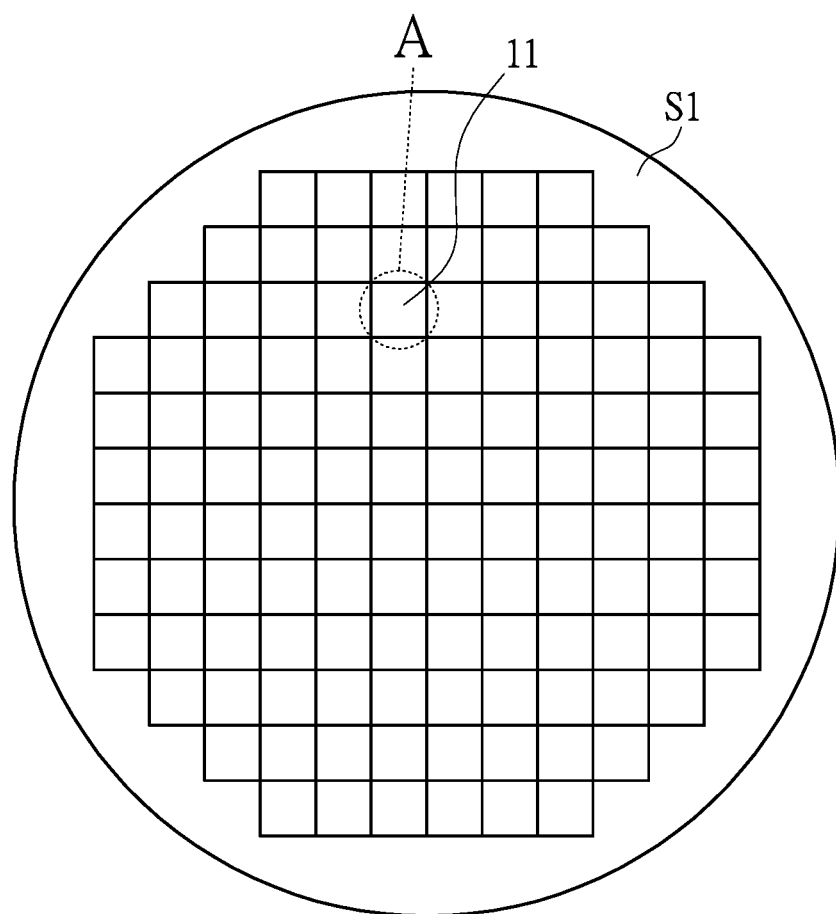
FIG. 5 shows a top view of a wafer in step S100 of FIG. 4 in accordance with another embodiment of the instant disclosure.
Figure 5A:
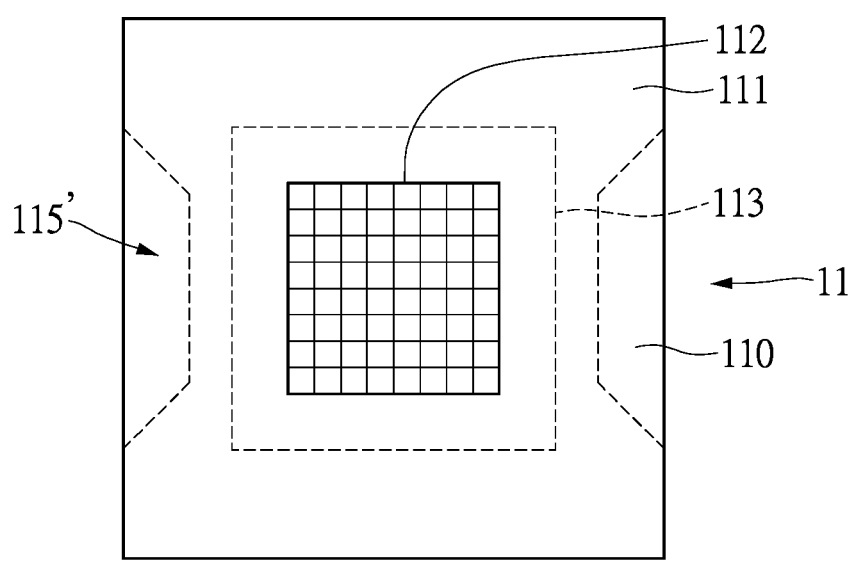
FIG. 5A shows an enlarged view of region A shown in FIG. 5.

Please refer to FIGS. 5 and 5A. FIG. 5 shows a top view of a wafer in step S100 of FIG. 4 in accordance with another embodiment of the instant disclosure and FIG. 5A shows an enlarged view of region A shown in FIG. 5.

The wafer S1 is usually made of silicon, or the other semiconductor materials, such as gallium arsenide, gallium nitride, or silicon carbide. In the instant embodiment, the fabrication process of devices has been performed on the wafer S1 so that the wafer S1 has a plurality of the sensor chips 11, and each sensor chip 11 includes an active region 112 and a wiring region 113 surrounding the active region 112, and at least one pre-thinned region 115' (two pre-thinned regions 115' shown in FIG. 5).

Furthermore, a control circuit has been formed in the wiring region 113, and each pre-thinned region 115' is positioned at one side of the active region 112. The coverage of each pre-thinned region 115' extends to one of boundary lines of the sensor chip 11.

Please refer to FIG. 4. Subsequently, in step S101, the pre-thinned region of each sensor chip is etched to form a concave portion positioned at one side of the active region 112 of each sensor chip 11.

Figure 6A:
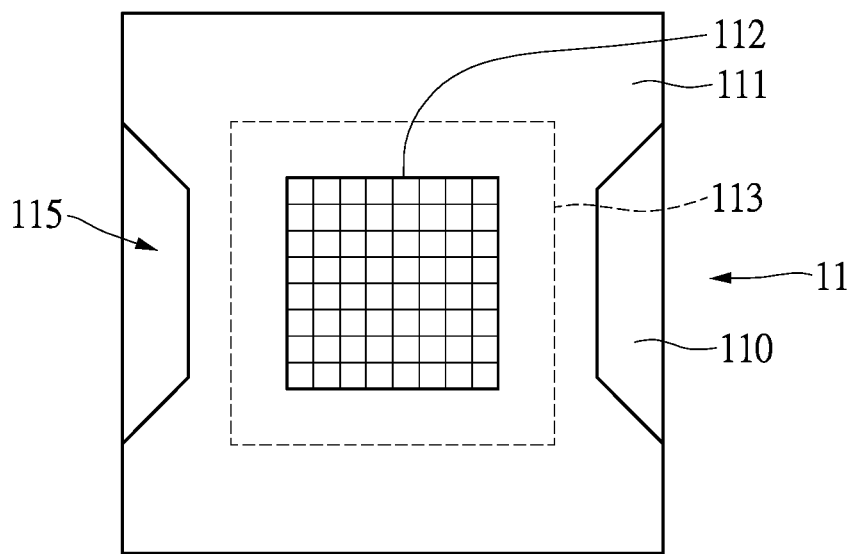
FIG. 6A shows a top view of one of the sensor chips in step S101 of FIG. 4 in accordance with an embodiment of the instant disclosure.
Figure 6B:
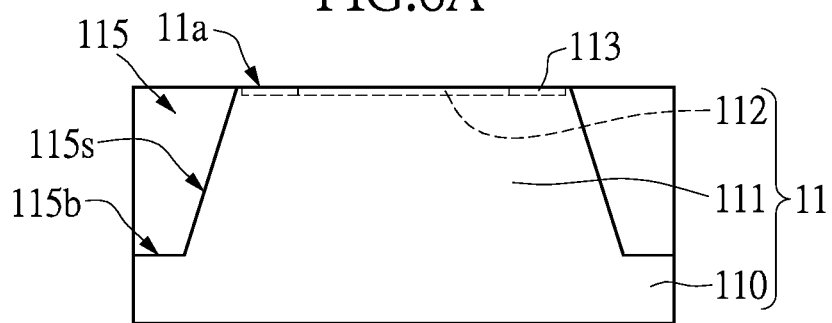
FIG. 6B shows a sectional view of the sensor chip shown in FIG. 6A.

Please refer to FIGS. 6A and 6B. FIG. 6A shows a top view of one of sensor chips in step S101 of FIG. 4 in accordance with an embodiment of the instant disclosure. FIG. 6B shows a sectional view of the sensor chip shown in FIG. 6A.

As shown in FIG. 6B, after the pre-thinned regions 115' are etched, the concave portions 115 depressed from the top surface 11a are formed. In addition, each concave portion 115 has a sidewall surface 115s and a bottom surface 115b, and the sidewall surface 115s connected between the top surface 11a and the bottom surface 115b is an inclined surface. In the instant embodiment, one of the concave portions 115 has a depth ranging from 100 to 400 μm. The formation of the concave portion 115 at the pre-thinned region 115' can be carried out by performing a wafer-level etching process, which may include the well-known steps of photoresist coating, exposure, development, etching and photoresist removal, and so on.

That is to say, after the abovementioned etching step, each sensor chip 11 includes a base portion 110 and a protruding portion 111 protruding from an upper surface of the base portion 110. The active region 112 and wiring region 113 is positioned at the top surface (i.e., top surface 11a) of the protruding portion 111. In addition, a portion of the upper surface of the base portion 110 not covered by the protruding portion 111 is the bottom surface 115b of the concave portion 115. The protruding portion 111 has at least one inwardly sidewall surface, that is, the sidewall surface 115s of the concave portion 115. Furthermore, the protruding portion 111 has a height relative to the upper surface of the base portion 110 that is equal to the depth of the concave portion 115.

Figure 6C:
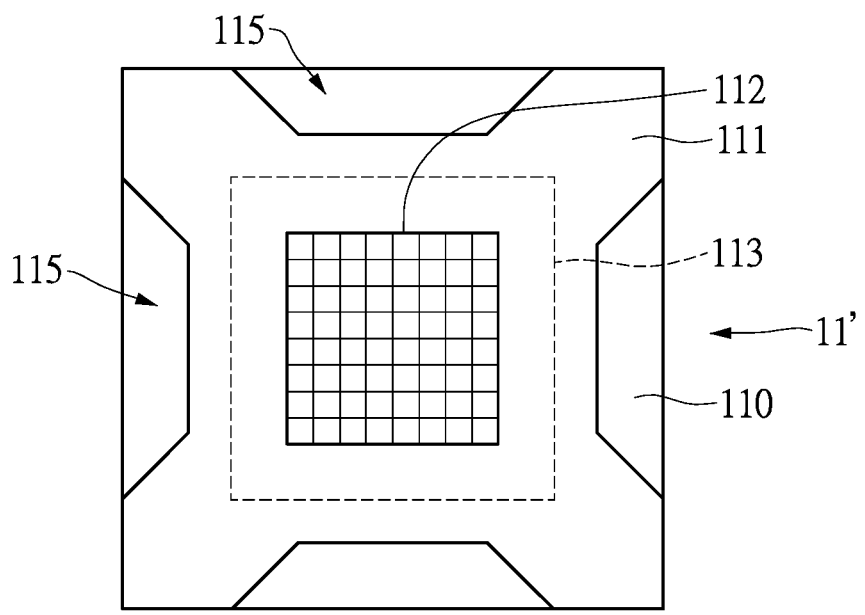
FIG. 6C shows a top view of one of the sensor chips in step S101 of FIG. 4 in accordance with another embodiment of the instant disclosure.

In the embodiment shown in FIG. 6A, each sensor chip 11 includes two concave portions 115 respectively formed at two opposite sides of the active region 112. In another embodiment as shown in FIG. 6C, each sensor chip 11' can include four concave portions 115 according to practical demands, and the four concave portions 115 respectively extend transversely through four boundary lines of the corresponding sensor chip 11'. In another embodiment, the sensor chip 11 can have only one concave portion 115, and the number of the concave portion 115 is not limited to the example provided herein.

Figure 7A:
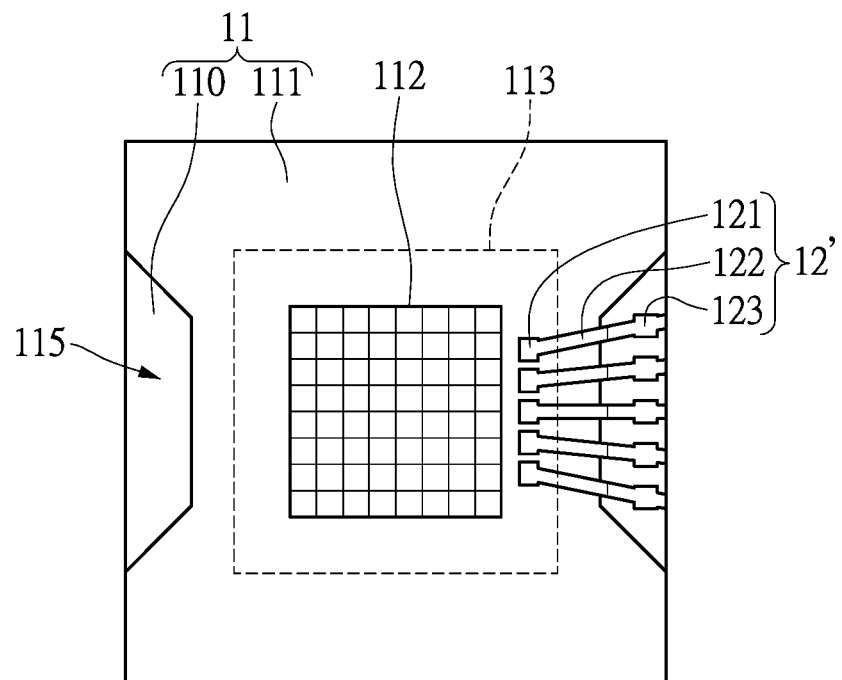
FIG. 7A shows a top view of one of the sensor chips in step S102 of FIG. 4 in accordance with an embodiment of the instant disclosure.

Please refer to FIG. 4. In step S102, a redistribution layer is formed on the wafer. Please refer to FIG. 7A and FIG. 7B. FIG. 7A shows a top view of one of the sensor chips in step S102 of FIG. 4 in accordance with an embodiment of the instant disclosure, and FIG. 7B shows a sectional view of the sensor chip shown in FIG. 7A.

Figure 7B:
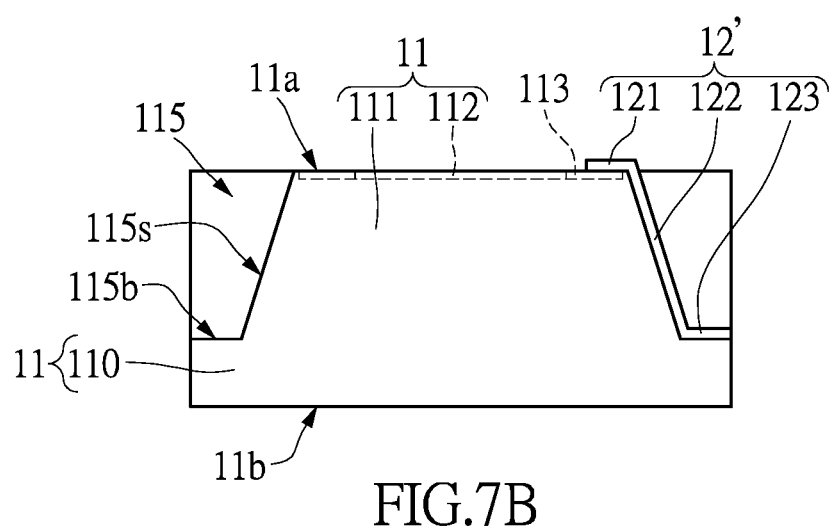
FIG. 7B shows a sectional view of the sensor chip shown in FIG. 7A.

As shown in FIGS. 7A and 7B, the redistribution layer 12' is formed on the top surface 11a of each sensor chip 11, the sidewall surface 115s and the bottom surface 115b of the concave portion 115. The redistribution layer 12' includes a plurality of first contact pads 121 disposed on the top surface 11a, a plurality of second contact pads 123 disposed on the bottom surface 115b of the concave portion 115, and a plurality of wires 122. Each wire 122 is connected between each first contact pad 121 and each second contact pad 123.

As shown in FIG. 7B, the first contact pad 121 is disposed on the top surface 11a of the sensor chip 11 and electrically connected to the control circuit formed in the wiring region 113. The second contact pad 123 is disposed on the bottom surface 115b of the concave portion 115, and at least a portion of the wire 122 extends from the first contact pad 121 disposed on the top surface 11a along the sidewall surface 115s of the concave portion 115 to the second contact pad 123 disposed on the bottom surface 115b.

The step of forming the redistribution layer 12' can be carried out by performing a lithography process. It is worth noting that the lithography process includes the steps of exposure and development, and the sidewall surface 115s of the concave portion 115 is an inclined plane, which can ensure the sidewall surface 115s can be completely impinged upon during the steps of exposure and development. As such, the wire 122 can be formed without breaks to ensure the electrical connection between the first and second contact pads 121, 123 can be established.

Additionally, in the following process, the active region 112 can be electrically connected to the traces or circuit of the substrate 10 through the plurality of the second contact pads 123 disposed on the bottom surface 115b of the concave portion 115. Accordingly, the redistribution layer 12' can be made of the metal or alloy which is easily bonded with the pads 100 disposed on the substrate 10, such as nickel, tin, silver or alloys thereof.

Please refer to FIG. 4. Subsequently, in step S103, a dam is formed on each sensor chip, in which the dam surrounds the active region and defines an enclosed opening.

Figure 8A:
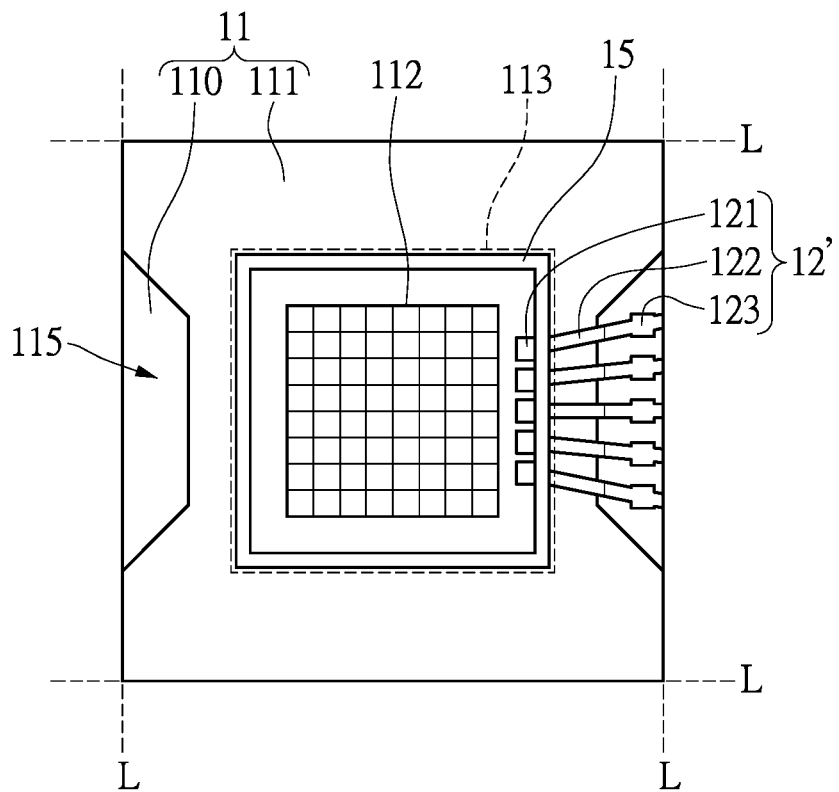
FIG. 8A shows a top view of one of the sensor chips in step S103 of FIG. 4 in accordance with an embodiment of the instant disclosure.
Figure 8B:
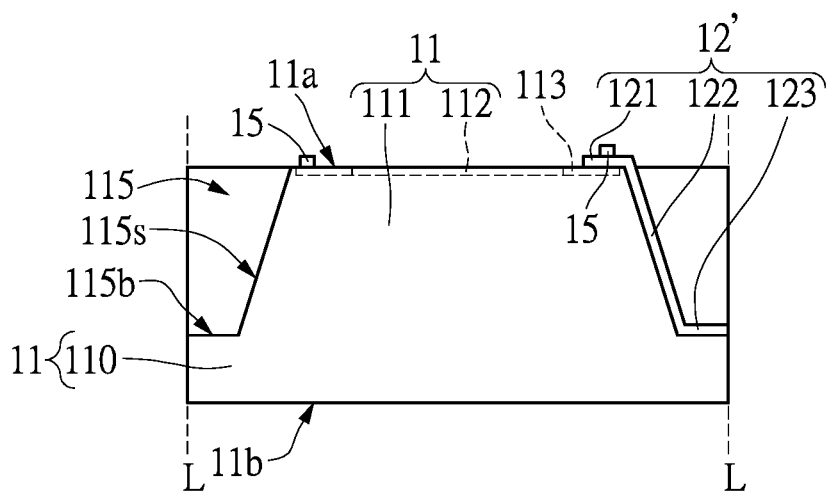
FIG. 8B shows a sectional view of the sensor chip shown in FIG. 8A.

Please refer to FIG. 8A and FIG. 8B. FIG. 8A shows a top view of one of the sensor chips in step S103 of FIG. 4 in accordance with an embodiment of the instant disclosure, and FIG. 8B shows a sectional view of the sensor chip shown in FIG. 8A.

As shown in FIG. 8A and FIG. 8B, the dam 15 is formed on top surface 11a of each sensor chip 11 and surrounds the active region 112. In one embodiment, the dam 15 is made of photo-imageable material. Therefore, the dam 15 can be formed by the steps of photoresist coating, exposure and development. The dam 15 has a height ranging from 2 to 50 μm, and a width (W) ranging from 5 to 100 μm.

In the instant embodiment, the dam 15 is stacked on a portion of the redistribution layer 12'. Accordingly, the step of forming the dam 15 is performed after the step of forming the redistribution layer 12'. In another embodiment, the sequence of the steps of forming the dam 15 and the redistribution layer 12' is not intended to limit the instant disclosure.

Subsequently, please refer to FIG. 4, which shows in step S104, a cutting process is performed on the wafer to form a plurality of separated sensor chips, in which at least a portion of a wiring layer is disposed on the separated sensor chip and extends from the active region along the sidewall surface to the bottom surface of the concave portion.

Please refer to FIG. 8A and FIG. 8B. When the cutting process is performed on the wafer S1 (as shown in FIG. 5), the wafer S1 is cut along a plurality of cutting lines (L) intersecting with each other to separate the sensor chips 11 from each other. Notably, after the cutting process, the redistribution layer 12' is cut so as to form a plurality of wiring layers 12 respectively formed on the separated sensor chips 11. Similar to the redistribution layer 12', each wiring layer 12 may include a plurality of first contact pads 121, a plurality of second contact pads 123 and a plurality of wires 122, and each of wire 122 is connected between the corresponding first and second contact pads 121, 123. The position and functions of the wiring layer 12 are omitted herein.

Figure 9A:
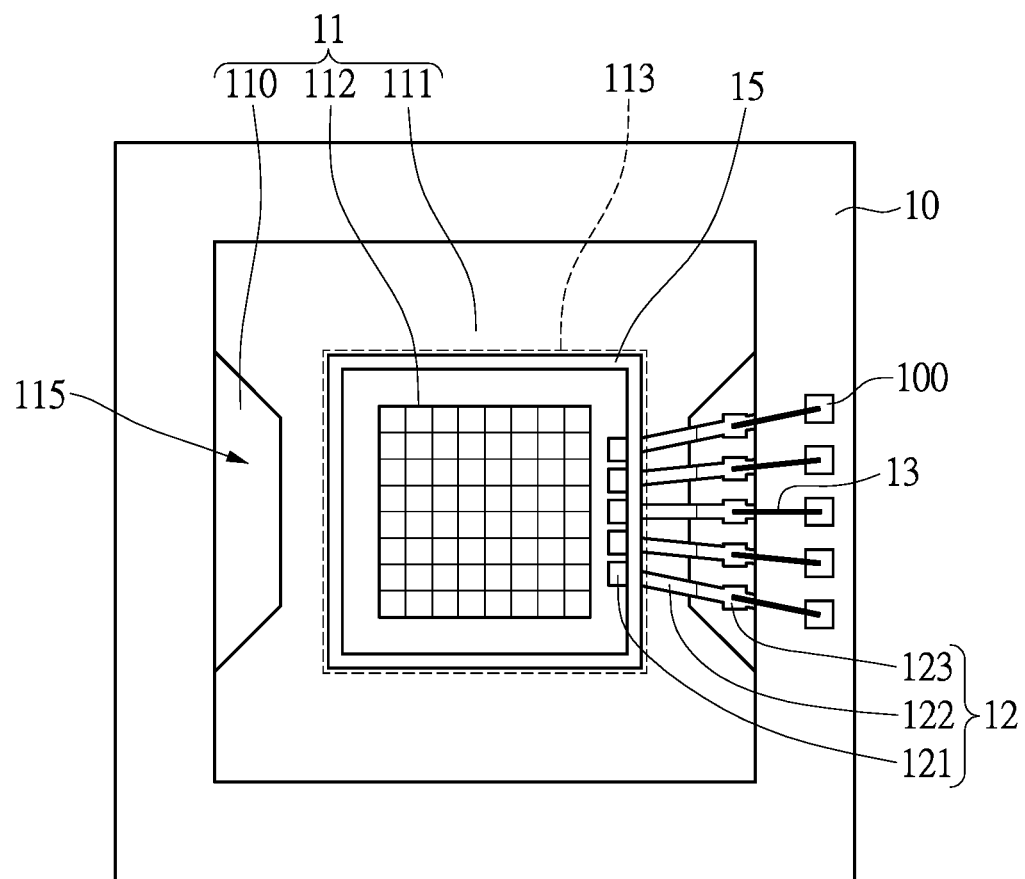
FIG. 9A shows a top view of one of the sensor chips in step S105 of FIG. 4 in accordance with an embodiment of the instant disclosure.
Figure 9B:
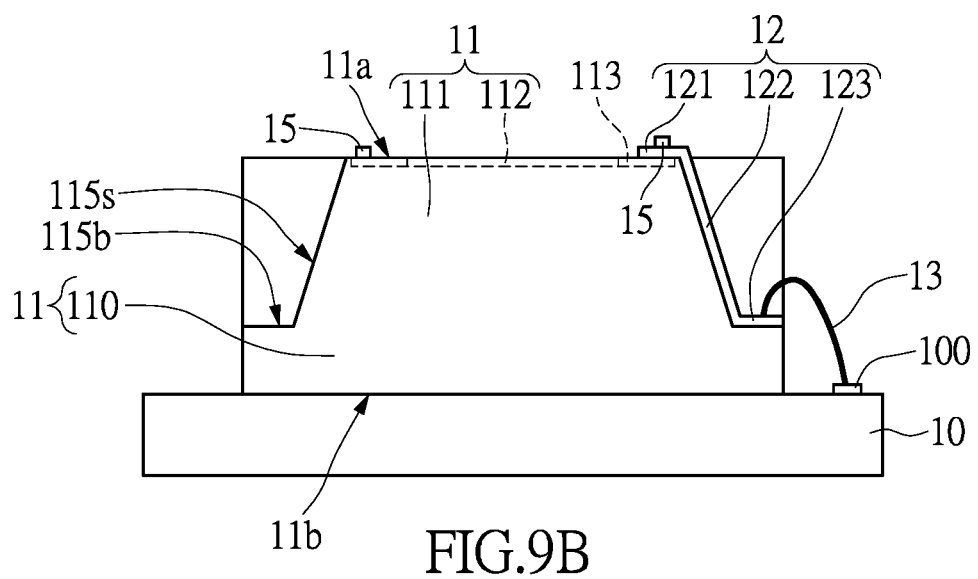
FIG. 9B shows a sectional view of the sensor chip shown in FIG. 9A.

Please refer to FIG. 4. Subsequently, in step S105, a plurality of separated sensor chips are respectively disposed on a plurality of substrate, and the active region of one of the sensor chips is electrically connected to the substrate. Please refer to FIG. 9A and FIG. 9B. FIG. 9A shows a top view of one of sensor chips in step S105 of FIG. 4 in accordance with an embodiment of the instant disclosure, and FIG. 9B shows a sectional view of the sensor chip shown in FIG. 9A.

Specifically, as shown in FIG. 9A, a plurality of traces and pads 100 have been configured on the substrate 10, and the separated sensor chip 11 is mounted on a predetermined position of the substrate 10.

In one embodiment, the second contact pads 123 are respectively electrically connected to the corresponding pads 100 through the bonding wires 13 by performing a wire bonding process. As mentioned above, the wiring layer 12 is electrically connected to the control circuit formed in the wiring region 113 so that the pads 100 on the substrate 10 are electrically connected to the active region 112.

Please refer to FIG. 4. In step S106, a molding compound is formed to encapsulate the substrate, the sensor chip and the wiring layer, in which the molding compound exposes the active region.

In one embodiment, the molding compound is formed by performing a transfer molding process. Notably, during the transfer molding process, the substrate 10 and the sensor chip 11 are placed commonly in the mold, and the epoxy molding compound is injected into the mold. The process of forming the molding compound is formed after the epoxy molding compound is cured.

Figure 10A:
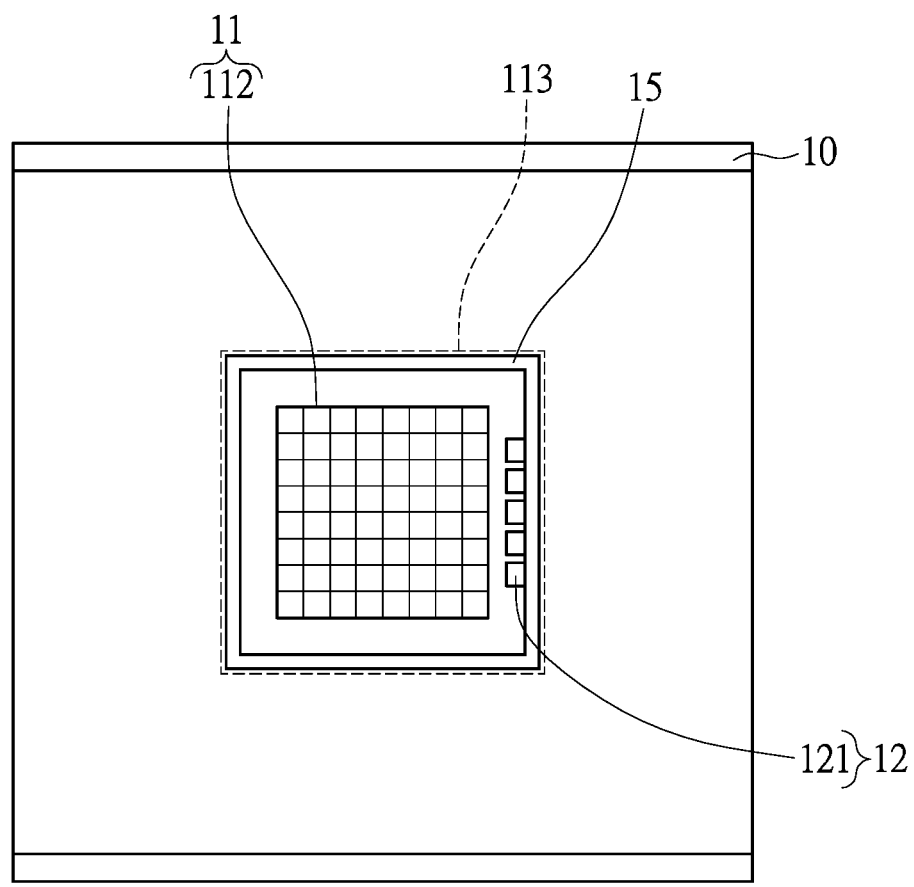
FIG. 10A shows a top view of one of the sensor chips in step S106 of FIG. 4 in accordance with an embodiment of the instant disclosure.
Figure 10B:
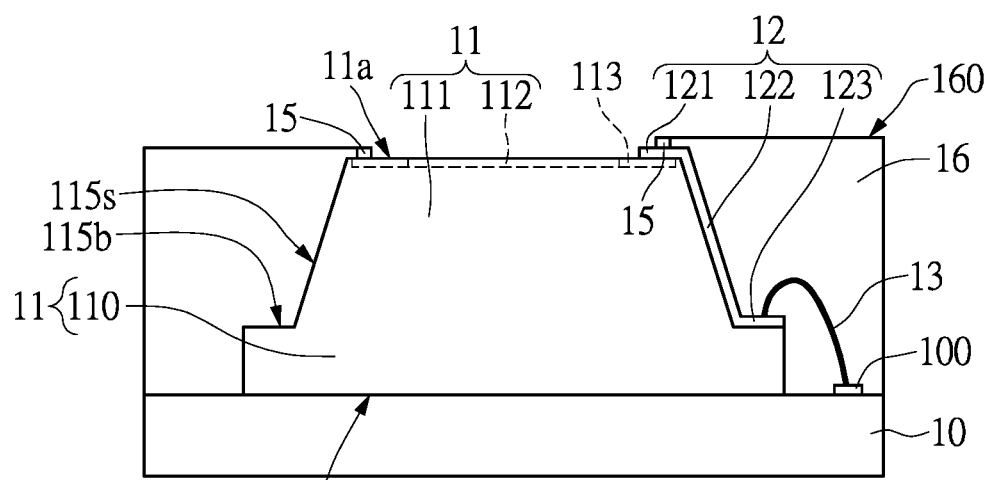
FIG. 10B shows a sectional view of the sensor chip shown in FIG. 10A.

Please refer to FIG. 10A and FIG. 10B. FIG. 10A shows a top view of one of sensor chips in step S106 of FIG. 4 in accordance with an embodiment of the instant disclosure, and FIG. 10B shows a sectional view of the sensor chip shown in FIG. 10A.

Notably, when the mold is injected into the epoxy molding compound, the dam 15 formed in step S103 can prevent the epoxy molding compound from flowing and covering the active region 112. Accordingly, a top face 160 of the molding compound 16 would be coplanar with (as shown in FIG. 10B) or lower than an end face of the dam 15. Therefore, the active region 112 of the sensor chip 11 would be exposed to the external environment through the enclosed opening defined by the dam 15 rather than covered by the molding compound 16.

Furthermore, in the instant embodiment, because the bonding wire 13 is directly connected to the second contact pad 123 positioned at the bottom surface 115b of the concave portion 115 and electrically connected to the active region 112 through the wire 122, a top point of the bonding wire 13 would be lower than a level where the top surface 11a of the sensor chip 11 is located. Additionally, since the top face 160 of the molding compound 16 is coplanar with the top end of the dam 15, the molding compound 16 can encapsulate the bonding wire 13.

In another embodiment, the sensor chip 11 and the substrate 10 can be packaged by other means. For example, during injecting into the epoxy molding compound, a cover having an opening can be provided to cover the sensor chip 11 and the substrate 10 and make the active region 112 be exposed through the opening to achieve the same results. Under these conditions, the step S103 can be omitted, i.e., the dam 15 is alternately formed on the top surface 11a of the sensor chip 11.

In another embodiment, after the step S102, the manufacturing method of the sensor chip package structure can further include arranging a light-emitting element in the concave portion.

Figure 11A:
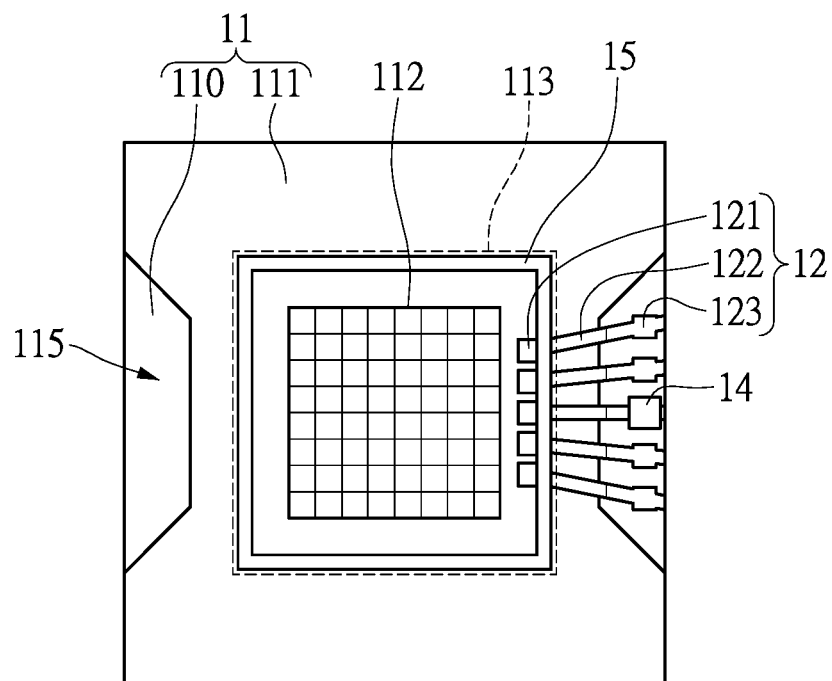
FIG. 11A shows a top view of one of the sensor chips in a step of the manufacturing method in accordance with another embodiment of the instant disclosure.
Figure 11B:
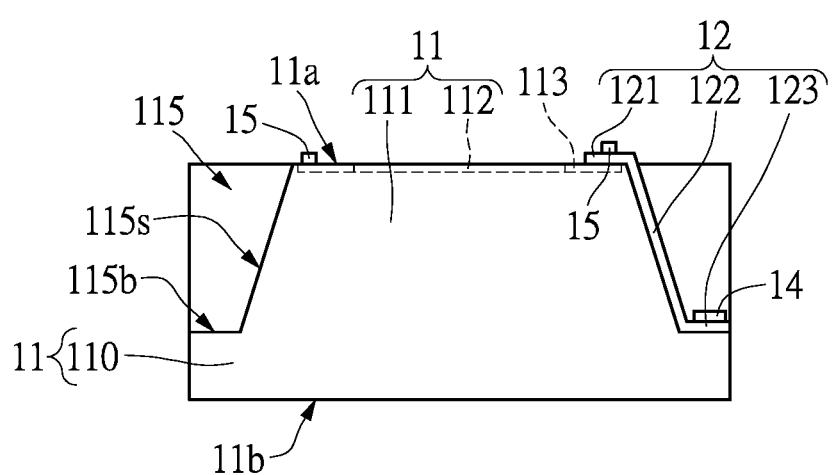
FIG. 11B shows a sectional view of the sensor chip shown in FIG. 11A.

Specifically, please refer to FIG. 11A and FIG. 11B, in which FIG. 11A shows a top view of one of sensor chips in a step of the manufacturing method in accordance with another embodiment of the instant disclosure, and FIG. 11B shows a sectional view of the sensor chip shown in FIG. 11A.

In the embodiment shown in FIGS. 11A and 11B, the light-emitting element 14 is disposed on the bottom surface 115b of the concave portion 115. In addition, the light-emitting element 14 has a thickness less than a depth of the concave portion. Furthermore, when the light-emitting element 14 has a ground terminal disposed on the bottom, the light-emitting element 14 can be stacked on one of the second contact pads 123 electrically connected to ground. That is to say, the second contact pads 123 where the light-emitting element 14 is stacked is a ground pad, and the wire 122 and the first contact pad 121 which are connected to the ground pad are mated with each other to form a grounding circuit.

In another embodiment, when both the ground terminal and the voltage input terminal of the light-emitting element 14 are disposed on a top portion of the light-emitting element 14, the light-emitting element 14 can be disposed on the bottom surface 115b of the concave portion 115 instead of stacked on the second contact pad 123.

Figure 12A:
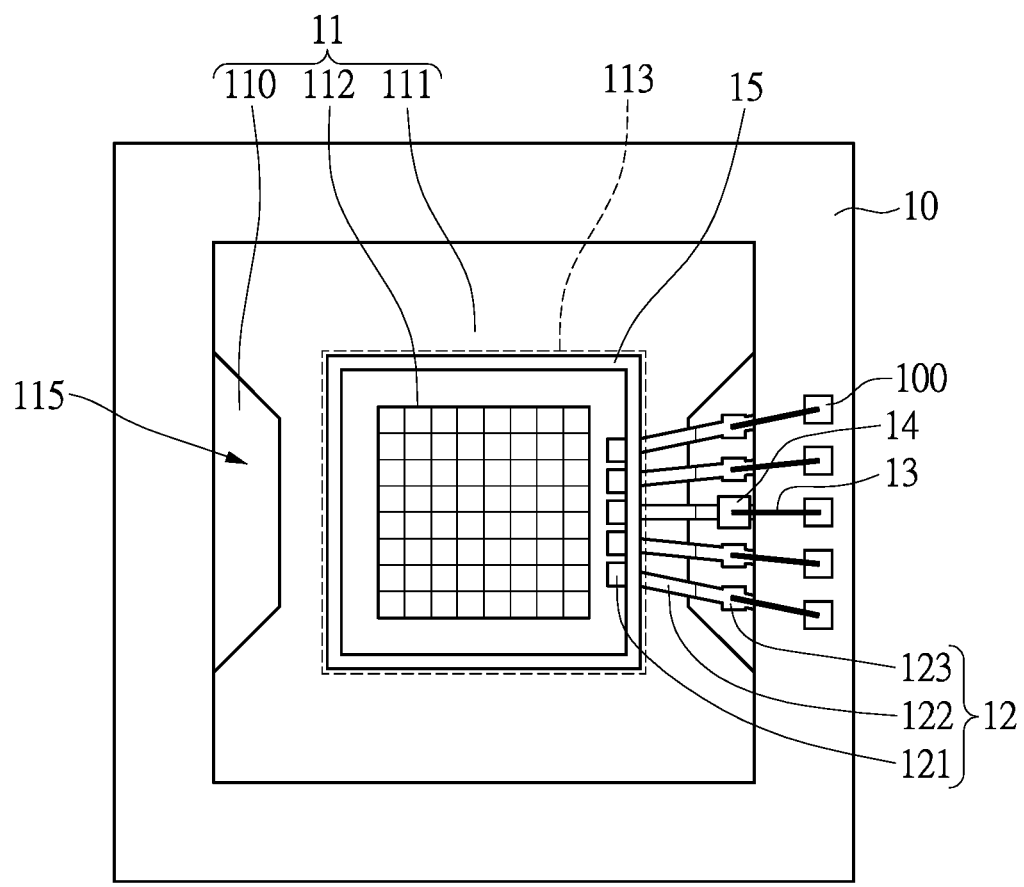
FIG. 12A shows a top view of one of sensor chips in a step of the manufacturing method in accordance with another embodiment of the instant disclosure.
Figure 12B:
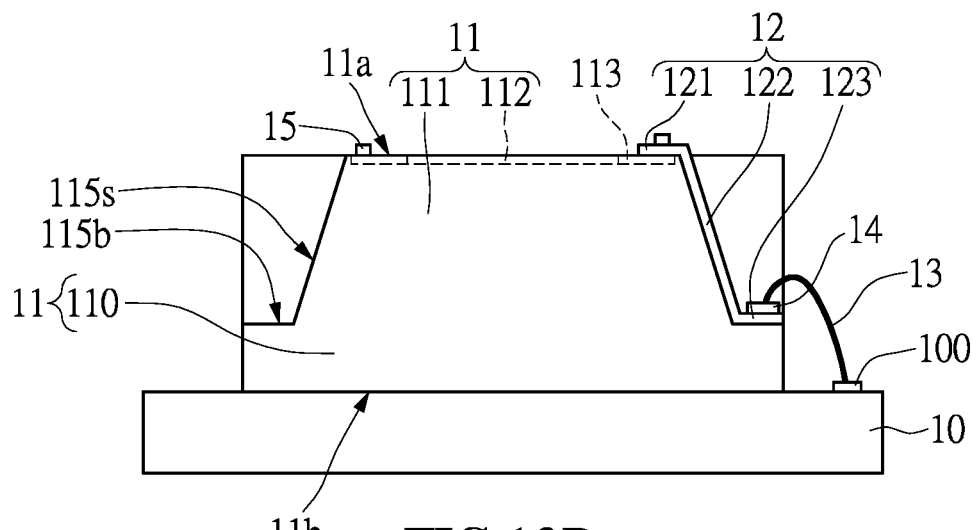
FIG. 12B shows a sectional view of the sensor chip shown in FIG. 12A.

After the light-emitting element 14 is arranged in the concave portion 115, a cutting process is performed on the wafer to form a plurality of separated sensor chips 11. Subsequently, please refer to FIGS. 12A and 12B. FIG. 12A shows a top view of one of sensor chips in a step of the manufacturing method in accordance with another embodiment of the instant disclosure, and FIG. 12B shows a sectional view of the sensor chip shown in FIG. 12A.

As illustrated in FIG. 12A, the sensor chip 11 and the light-emitting element 14 disposed thereon are disposed on the substrate 10. During the step of disposing the sensor chip 11 on the substrate 10, the manufacturing method further includes forming at least one bonding wire 13 so that the light-emitting element 14 is electrically connected to the substrate 10. As shown in FIG. 12B, the light-emitting element 14 is connected to the pad 100 of the substrate 10 through the bonding wire 13 such that an electrical connection between the light-emitting element 14 and a control circuit (ex: switching control circuit) can be established.

Figure 13A:
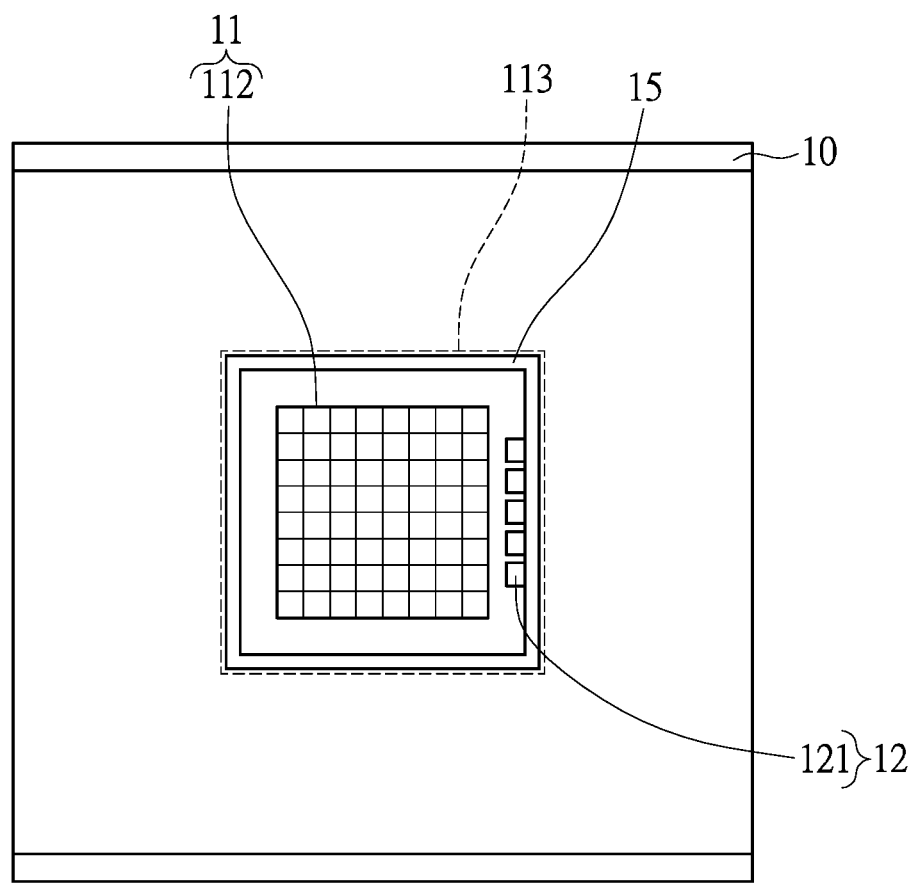
FIG. 13A shows a top view of one of sensor chips in a step of the manufacturing method in accordance with another embodiment of the instant disclosure.
Figure 13B:
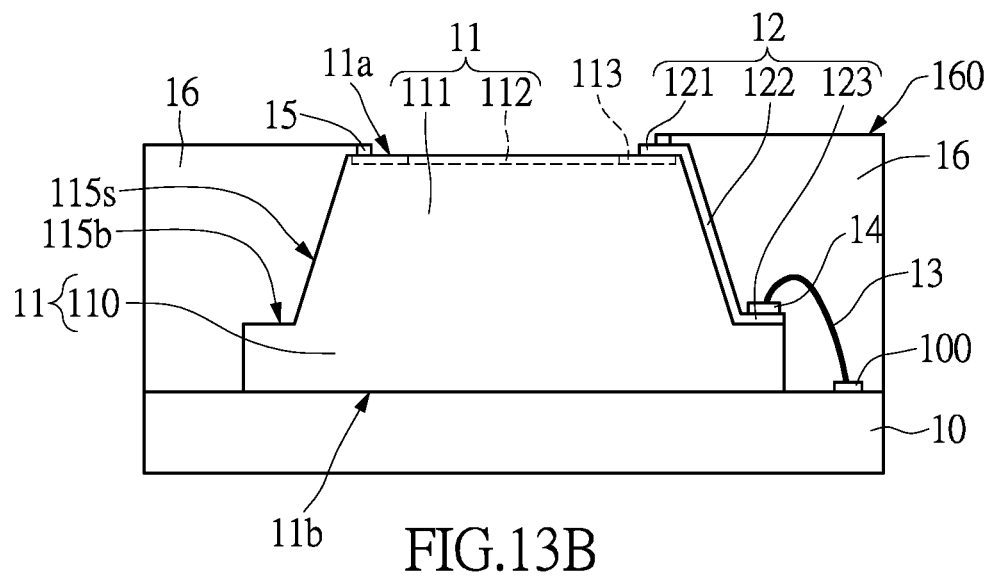
FIG. 13B shows a sectional view of the sensor chip shown in FIG. 13A.

Subsequently, please refer to FIGS. 13A and 13B, which respectively shows a top view of one of sensor chips in a step of the manufacturing method in accordance with another embodiment of the instant disclosure, and a sectional view of the sensor chip shown in FIG. 13A.

Similar to the step S106 shown in FIG. 4, the molding compound 16 is formed to encapsulate the substrate 10, the sensor chip 11, the light-emitting element 14, and the wiring layer 12, in which the molding compound exposes the active region 112 of the sensor chip 11.

Figure 14A:
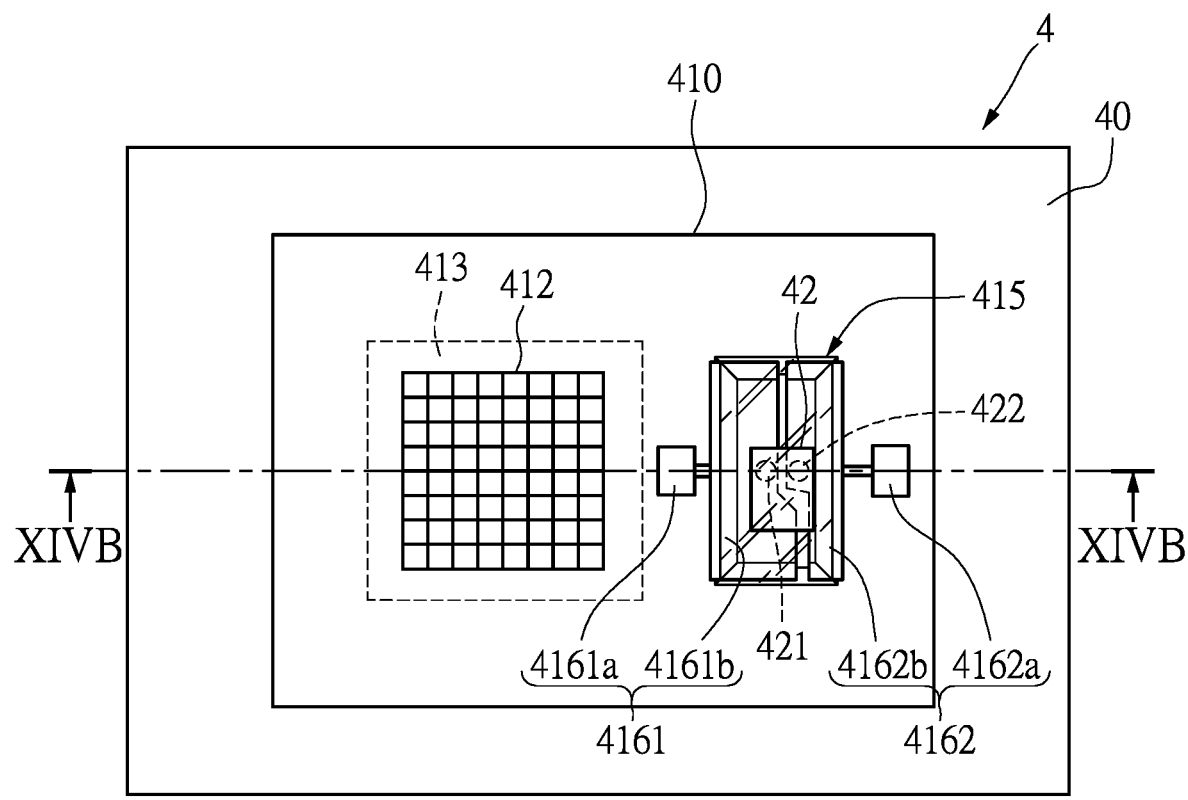
FIG. 14A shows a top view of an optical sensor module in accordance with an embodiment of the instant disclosure.
Figure 14B:
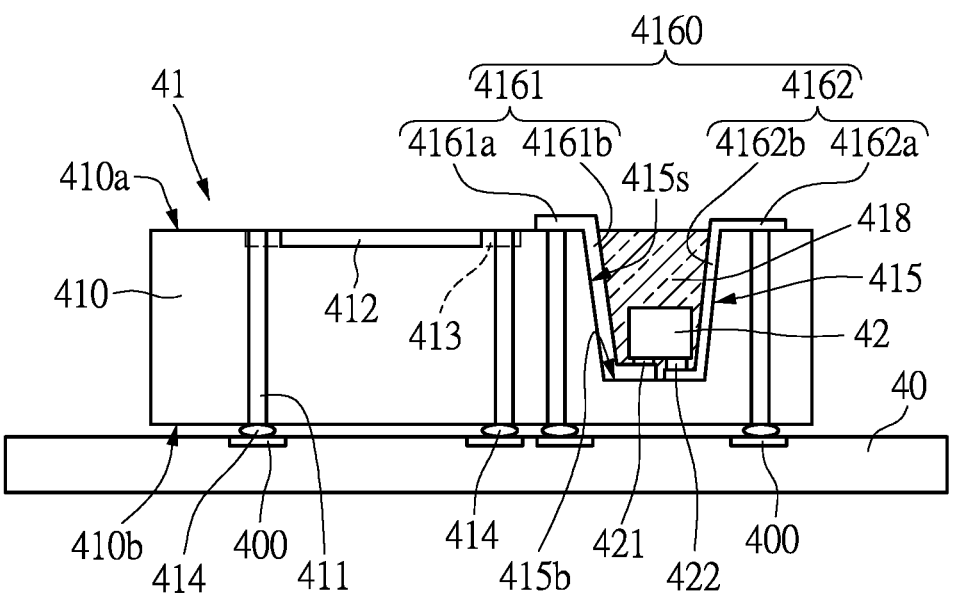
FIG. 14B shows a sectional view of the optical sensor module shown FIG. 14A.

Please refer to FIGS. 14A and 14B, which respectively shows a top view of an optical sensor module in accordance with another embodiment of the instant disclosure, and a sectional view of the sensor chip shown in FIG. 14A.

The optical sensor module 4 includes a substrate 40, a sensor chip 41, and a passive chip 42. The substrate 40 can be a metal plate, an insulating plate, or a composite plate, in which the composite plate may be a printed circuit board (PCB) or a flexible printed circuit (FPC). In the instant embodiment, the substrate 40 is a printed circuit board, the substrate 40 has a plurality of traces (not shown in FIG. 14A) embedded therein and a plurality of pads 400 disposed thereon, in which the pads 400 can be arranged according to the position of the sensor chip 41.

As shown in FIG. 14A and FIG. 14B, the sensor chip 41 is disposed on the substrate 40. The sensor chip 41 includes a chip body 410 and a multi-functional structure 416 disposed on the chip body 410.

The chip body 410 has a top surface 410a and a lower surface 410b opposite to the top surface 410a. In addition, the chip body 410 includes an active region 412 and a wiring region 413. The active region 412 is located at a top side of the chip body 410 and exposed at the top surface 41a. The wiring region 413 located at the top side of the chip body 410 surrounds the active region 412. A control circuit, which is electrically connected to the active region 412, has been laid out in the wiring region 413 to receive the signal detected by the active region 412.

In the instant embodiment, the sensor chip 41 is electrically connected to the pads 400 of the substrate 40 by flip-chip bonding. That is to say, the sensor chip 41 includes a plurality of internal conductive plugs 411 penetrating through the chip body 410 and a plurality of flip-chip pads 414 respectively corresponding to the internal conductive plugs 411 and mounted at the lower side of the chip body 410. The active region 412 is electrically connected to the substrate 40 through the internal conductive plugs 411 and the corresponding flip-chip pads 414. In one embodiment, the internal conductive plugs 411 can be formed by through silicon via process.

Furthermore, the chip body 410 has at least one recess portion 415 depressed from the top surface 410a thereof. In the instant embodiment, the recess portion 415 has a sidewall surface 415s and a bottom surface 415b, and the sidewall surface 415s is an inclined surface, which is connected between the top surface 410a and the bottom surface 415b. In the instant embodiment, one of the recess portions 415 has a depth D less than a thickness T of the chip body 410.

Additionally, the recess portion 415 is positioned at one side of the active region 412 and spaced from all of side surfaces of the chip body 410. Specifically, the recess portion 415 is enclosed within the chip body 410. Furthermore, the recess portion 415 is spaced from the active region 412 by a distance ranging from 0.5 cm to 1 cm. In another embodiment, the recess portion 415 extends elongatingly toward two opposite edges of the chip body 410 or the recess portion 415 extends toward one edge of the chip body 410 and opens outwardly.

In the instant embodiment, the recess portion 415 is configured to accommodate the passive chip 42 so that the distance between the active region 12 and the passive chip 42 can be reduced. Additionally, the depth D of the recess portion 415 is greater than a thickness of the passive chip 42. That is to say, when the passive chip 42 is accommodated in the recess portion 415, a top end of the passive chip 42 does not protrude from the top surface 410a of the chip body 410. As such, even if the sensor chip 41 is equipped with the passive chip 42, the size of the sensor chip 41 does not increase due to the passive element 42. In other words, by placing the passive chip 42 in the recess portion 415, the optical sensor module 4 has a smaller size.

The passive chip 42 can be a light-emitting component for emitting light projecting on an object to be tested. The active region 412 receives the reflected light reflected off the object to form an image of the object and for identification. The light-emitting component can be an LED or a laser diode for generating a monochromatic light or a polychromatic light, such as visible light, UV light, or infrared light.

As shown in FIG. 14B, the multi-functional structure 416 is disposed on an inner surface of the recess portion 415 for electrically connecting the passive chip 42 to the substrate 40.

Specifically, the multi-function structure 416 can include a redistribution layer 4160 disposed on the top surface 410a of the chip body 410, the sidewall surface 415s and the bottom surface 415b of the recess portion 415. In the instant embodiment, the redistribution layer 4160 includes a first conductive portion 4161 and a second conductive portion 4162, which are insulated from each other. In one embodiment, the first and second conductive portions 4161, 4162 are spaced by a gap to be insulated from each other, as shown in FIG. 14A. However, in another embodiment, the first and second conductive portions 4161, 4162 can be electrically insulated from each other by disposing an insulating layer therebetween. Accordingly, as long as the first and second conductive portions 4161, 4162 can be electrically insulated from each other, the instant disclosure is not so restricted.

In the embodiment shown in FIGS. 14A and 14B, the first conductive portion 4161 includes a first contact pad 4161*a* disposed on the top surface 410*a* and a first wiring layer 4161*b* extending from the first contact pad 4161*a* to the bottom surface 415*b* along one part of the sidewall surface 415*a*. Moreover, the first contact pad 4161*a* can be electrically connected to one of the pads 400 of the substrate 40 through the corresponding internal conductive plug 411.

Similarly, the second conductive portion 4162 includes a second contact pad 4162*a* disposed on the top surface 410*a* of the chip body 410 and a second wiring layer 4162*b* extending from the second contact pad 4162*a* to the bottom surface 415*b* along the other part of the sidewall surface 415*a*. The second contact pad 4162*a* can be electrically connected to another one of the pads 400 of the substrate 40 through the corresponding internal conductive plug 411.

In the instant embodiment, the passive chip 42 is electrically connected to the substrate 40 by flip-chip bonding. That is to say, the first terminal 421 and the second terminal 422 positioned at the bottom side of the passive chip 42 can be electrically connected to the substrate 400 without any bonding wire.

Specifically, when the passive chip 42 is disposed on the bottom surface 415*b* of the recess portion 415, the first terminal 421 and the second terminal 422, which are located at the bottom side of the passive chip 42, are respectively in contact with and bonded to a first wiring layer 4161*a* and the second wiring layer 4162*b*. Additionally, the substrate 40 includes a switching control circuit for controlling the passive chip 42, and the first terminal 421 and the second terminal 422 can be electrically connected to the switching control circuit through the internal conductive plugs 411, the flip-chip pads 414 and the pads 400.

In one embodiment, when the passive chip 42 is the light-emitting component for emitting infrared light, the redistribution layer 416 of the instant embodiment can be served as a shielding layer for preventing the active region 412 from receiving the light emitted by the light-emitting component. In other words, the redistribution layer 416 is not only used for electrically connecting the passive chip 42 to the substrate 40, but also for preventing the active region 412 from receiving light emitted by the passive chip 42.

Specifically, since silicon (the material of the chip body 410) is partially transparent to infrared light, the infrared light emitted by the light-emitting component may pass through the chip body 410 and then interfere with the normal signal received by the active region 412. Thus, the infrared light received by the active region 412 may result in higher signal noise and lower image identification accuracy. Accordingly, in the instant embodiment, at least one of the first wiring layer 4161*b* and the second wiring layer 4162*b* covers a portion of the sidewall surface 415*s* that is closest to the active region 412 so that the active region 412 is isolated from the infrared light. That is, at least one of the first wiring layer 4161*b* and the second wiring layer 4162*b* can be located between the light-emitting component (the passive chip 42) and the active region 412 to prevent the active region 412 from receiving the infrared light. In this case, the first wiring layer 4161*b* or the second wiring layer 4162*b* can be made of metal material, such as aluminum (Al) or chromium (Cr). In another embodiment, the first wiring layer 4161*b* or the second wiring layer 4162*b* can be designed to isolate the light with the wavelength falling within another range.

Furthermore, the redistribution layer 416 of the instant embodiment also can be served as a reflecting layer for reflecting the light emitted by the light-emitting component. Specifically, the first wiring layer 4161*b* and the second wiring layer 4162*b* commonly cover the sidewall surface 415*s* of the recess portion 415 with 80% to 90% surface area coverage. That is to say, the first wiring layer 4161*b* and the second wiring layer 4162*b* commonly surround the passive chip 42. Furthermore, each of the first wiring layer 4161*b* and the second wiring layer 4162*b* is a metal layer having a reflective surface for reflecting light emitted from the light-emitting component. As such, the functions of the recess portion 415 and the redistribution layer 416 are similar to that of a reflective cup so as to adjust the light emitting angle and increase the luminous efficacy of the light-emitting component.

Additionally, the sensor chip 41 further includes a protective material 418 disposed in the recess portion 415. The protective material 418 can be resin, such as epoxy, silicone, or the other materials. The protective material 418 in liquid state can be injected into the recess portion 415 until the protective material 418 completely covers the passive chip 42. Subsequently, the protective material 418 can be cured and encapsulate the passive chip 42 to protect the passive chip 42 from moisture. In one embodiment, when the passive chip 42 is the light-emitting component, the protective material 418 is transparent to the light emitted by the light-emitting component. In the instant embodiment, a top face (not labeled) of the protective material 418 can be coplanar with or be lower than the top surface 410*a* of the chip body 410.

Figure 15:
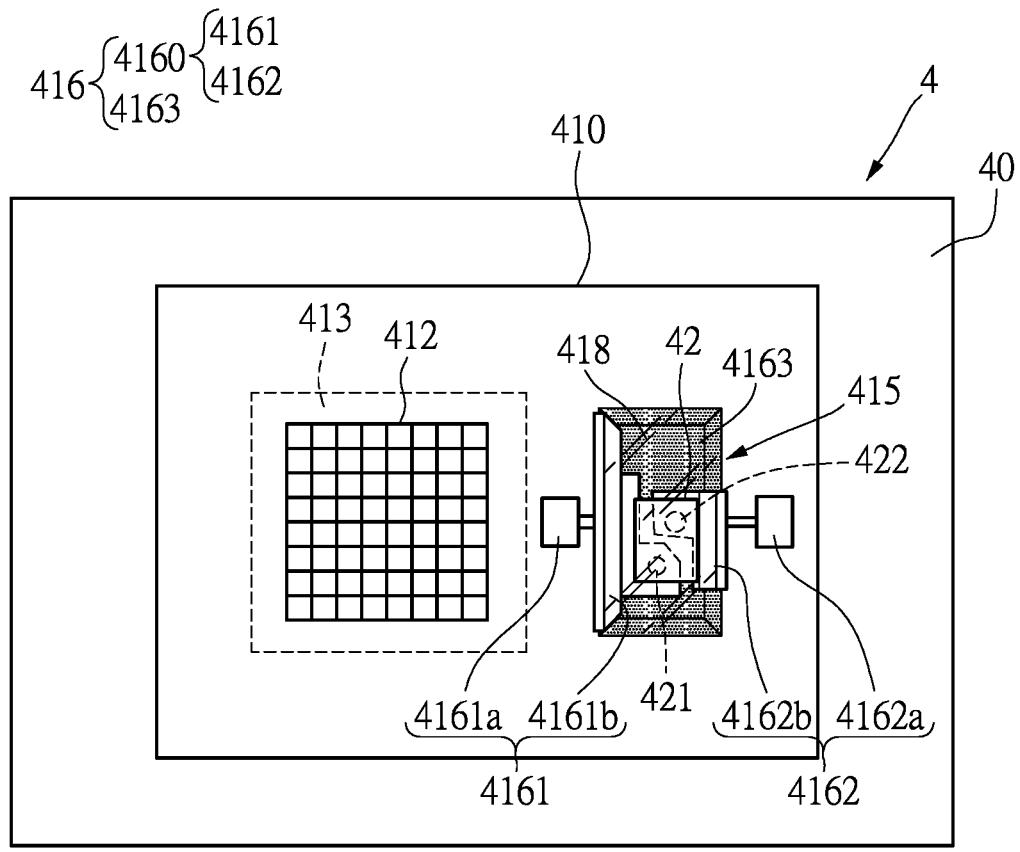
FIG. 15 shows a top view of an optical sensor module in accordance with another embodiment of the instant disclosure.

Please refer to FIG. 15. FIG. 15 shows a top view of an optical sensor module in accordance with another embodiment of the instant disclosure. As shown in FIG. 15, the multi-function structure 416 can further include a reflective layer 4163 disposed on the sidewall surface 415*s* of the recess portion 415 for reflecting light emitted by the light-emitting component (the passive chip 42).

Specifically, in the instant embodiment, the multi-function structure 416 includes the redistribution layer 4160 and a reflecting layer 4163. In the instant embodiment, the first wiring layer 4161*a* of the redistribution layer 4160 only covers a portion of the sidewall surface 415*s* that is located between the active region 412 and the passive chip 42 so as to prevent light emitted by the passive chip 42 from entering the active region 412. The reflecting layer 4163 covers the other portions of sidewall surface 415*s* which are not occupied by the first wiring layer 4161*b* and the second wiring layer 4162*b*. The reflecting layer 4163 of the instant embodiment is made of an insulator so that the first wiring layer 4161*b* and the second wiring layer 4162*b* are insulated from each other. In other words, the inner surface (including the sidewall surface 415*s* and the bottom surface 415*b*) of the recess portion 415 is completely covered by the first wiring layer 4161*b*, the second wring layer 4162*b* and the reflecting layer 4163.

Figure 16A:
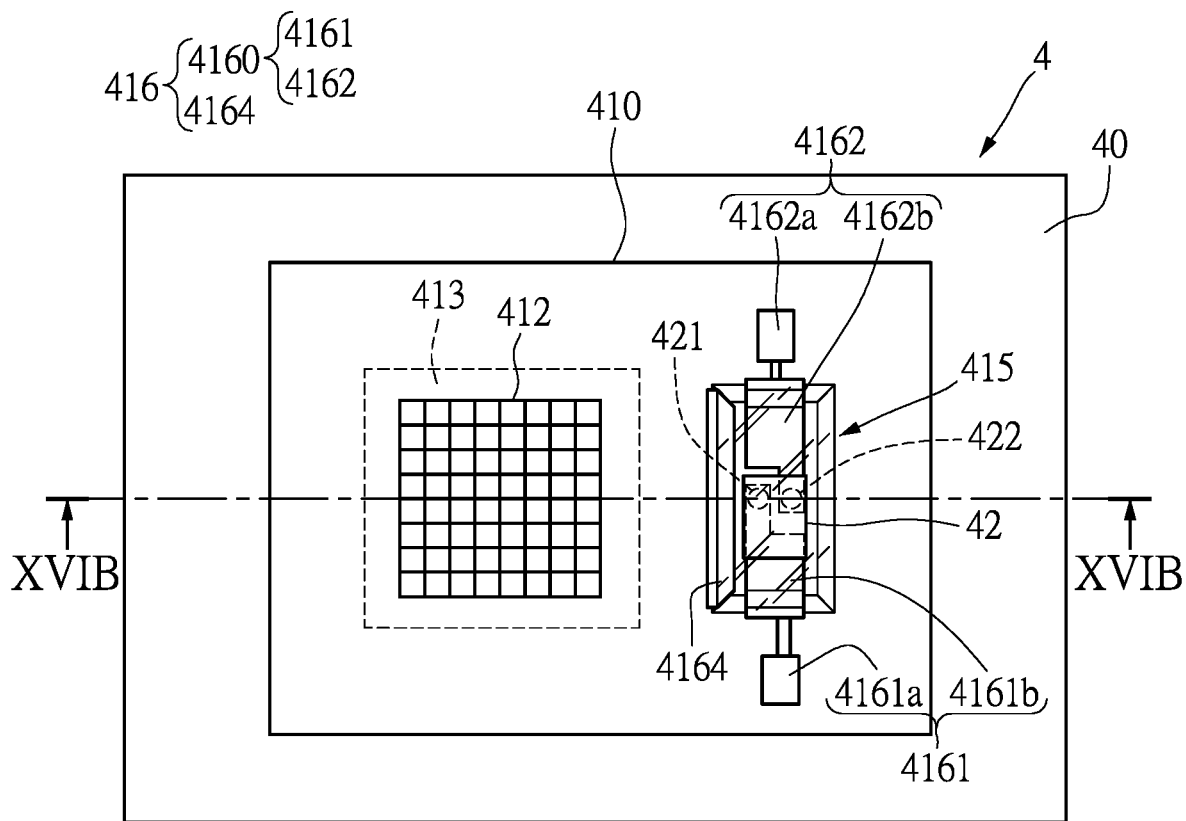
FIG. 16A shows a top view of an optical sensor module in accordance with another embodiment of the instant disclosure.
Figure 16B:
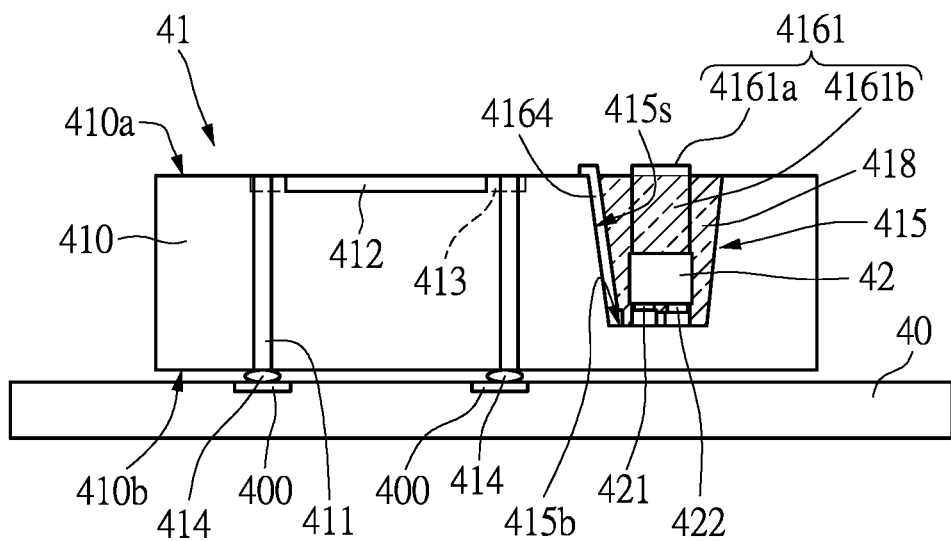
FIG. 16B shows a sectional view of the optical sensor module shown FIG. 16A.

Please refer to FIG. 16A and FIG. 16B. FIG. 16A shows a top view of an optical sensor module in accordance with another embodiment of the instant disclosure. FIG. 16B shows a sectional view of the optical sensor module shown FIG. 16A. In the instant embodiment, the multi-function structure 416 includes a shielding layer 4164 disposed on at least one portion of the sidewall surface 415*s* that is closest to the active region 412. The shielding layer 4164 can be made of the material that can be an insulator and substantially non-transparent to light emitted by the light-emitting component.

Figure 17A:
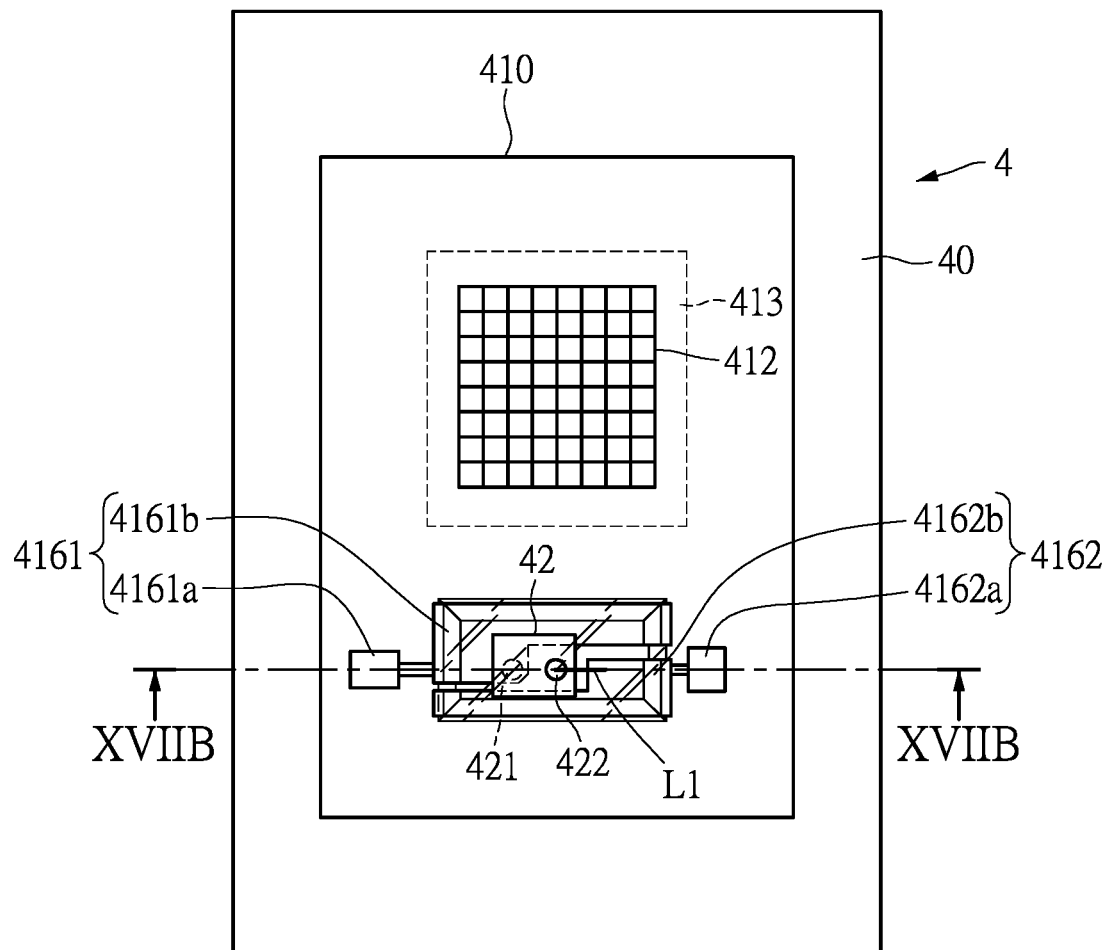
FIG. 17A shows a top view of an optical sensor module in accordance with an embodiment of the instant disclosure.
Figure 17B:
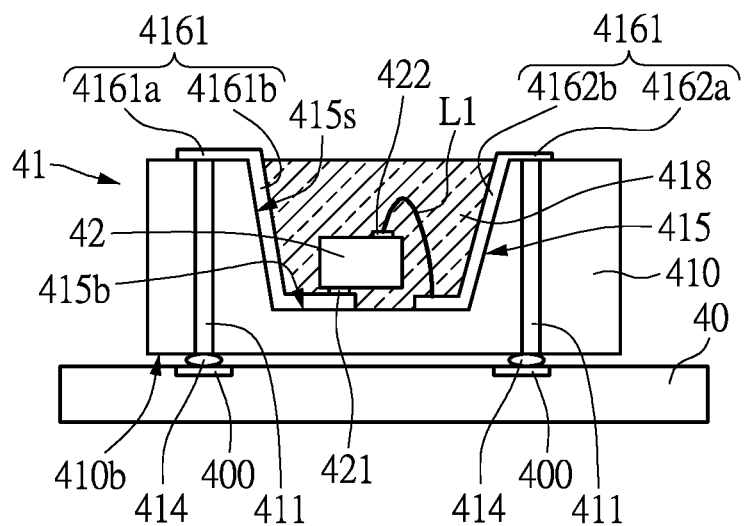
FIG. 17B shows a sectional view of the optical sensor module shown FIG. 17A.

Please refer to FIGS. 17A and 17B, which respectively shows a top view of an optical sensor module in accordance with another embodiment of the instant disclosure and a sectional view of the optical sensor module shown FIG. 17A.

In the instant embodiment, the first terminal 421 and the second terminal 422 of the passive chip 42 are respectively positioned at two opposite sides of the passive chip 42. Furthermore, the passive chip 42 is electrically connected to the substrate 40 by wire bonding.

Specifically, as shown in FIG. 17B, the first terminal 421 located at the bottom side of the passive chip 42 is directly in contact with the first wiring layer 4161a, and the second terminal 422 located at the top side of the passive chip 42 is electrically connected to the second wiring layer 4162b by a boning wire L1. Notably, the recess portion 415 has a larger space than that in the previous embodiment shown in FIG. 14A so as to provide a space for the bonding wire L1. Specifically, the bottom surface 415b of the recess portion 415 has an area larger than that in the previous embodiment shown in FIG. 14A. However, the size of the recess portion 415 should be limited such that the structural integrity of the sensor chip 41 will not be compromised thereby.

It is worth noting that in the prior art optical sensor module, both the light-emitting component and the chip are directly mounted on the substrate, and the distance between the light-emitting component and the sensing region of the chip cannot be further shortened due to the structural limitation of the chip.

In the instant embodiment, the passive chip 42 (or the light-emitting component) can be directly placed on the chip body 410 of the sensor chip 41 due to the formation of the recess portion 415 on the top surface 410a of the chip body 410. As such, the horizontal distance between the passive chip 42 and the active region 412 can be shortened so as to increase the image identification accuracy. In addition, since the sensor chip 41 is electrically connected to the substrate 40 by flip-chip bonding, instead of wiring boding, the molding compound, which is used in the previous embodiment shown in FIG. 3B to protect the bonding wire 13, can be omitted. As such, compared with the sensor chip package structure of the previous embodiment, the optical sensor module 4 of the instant embodiment has a smaller size.

To sum up, the sensor chip package structure and the manufacturing method thereof in accordance with the instant disclosure can make the active region be exposed to the external environment to be directly touched by an object, such as a finger. In addition, the sensor chip includes at least one concave portion depressed from the top surface so that the wiring layer can be disposed on the bottom surface and the sidewall surface of the concave portion to establish the electrical connection between the active region and the substrate.

Additionally, by forming the concave portion or the recess portion in the sensor chip, the light-emitting element or the passive chip can be directly disposed on the sensor chip. As such, the horizontal distance between the light-emitting element and the active region can be shortened, which is of benefit for improving the image identification accuracy. In addition, compared to the prior art sensor chip package, since the light-emitting element of the sensor chip package structure and the optical sensor module provided in the instant disclosure can be directly disposed on the sensor chip, the size of the sensor chip package structure and the optical sensor module can be smaller.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. An optical sensor module comprising:
   a substrate; and
   a sensor chip disposed on the substrate, wherein the sensor chip includes a chip body having an active region located at a top side thereof and a recess portion depressed from a top surface of the chip body; and
   a light-emitting component accommodated in the recess portion, wherein a depth of the recess portion is greater than a thickness of the light-emitting component;
   wherein the sensor chip further includes a multi-functional structure disposed on an inner surface of the recess portion, and the light-emitting component is electrically connected to the substrate by the multi-functional structure.

2. The optical sensor module according to claim 1, wherein the multi-functional structure includes at least one metal layer disposed on a sidewall surface of the recess portion and surrounding the light-emitting component for preventing the active region from receiving the light emitted by the light-emitting component, for electrically connecting the light-emitting component to the substrate, and for reflecting the light emitted by the light-emitting component.

3. The optical sensor module according to claim 1, wherein the multi-functional structure includes a shielding layer disposed on a sidewall surface of the recess portion and located between the light-emitting component and the active region for preventing the active region from receiving the light emitted by the light-emitting component.

4. The optical sensor module according to claim 1, wherein the multi-functional structure includes a redistribution layer for electrically connecting the light-emitting component to the substrate.

5. The optical sensor module according to claim 4, wherein the redistribution layer includes a first conductive portion and a second conductive portion insulated from each other.

6. The optical sensor module according to claim 5, wherein the light-emitting component has a first terminal and a second terminal, and the first terminal and the second terminal are respectively electrically connected to the first conductive portion and the second conductive portion by wire bonding or flip-chip bonding.

7. The optical sensor module according to claim 1, wherein the multi-functional structure includes a reflective layer disposed on a sidewall surface of the recess portion for reflecting light emitted by the light-emitting component.

8. The optical sensor module according to claim 1, wherein the sensor chip further comprises a protective material disposed in the recess portion for encapsulating the light-emitting component.

9. The optical sensor module according to claim 8, wherein the protective material is transparent to the light emitted by the light-emitting component.

10. The optical sensor module according to claim 1, wherein the recess portion is spaced from all of side surfaces of the chip body.

11. The optical sensor module according to claim 1, wherein the depth of the recess portion is less than a thickness of the chip body.

12. The optical sensor module according to claim 1, wherein the recess portion is spaced from the active region by a distance ranging from 0.5 cm to 1 cm.

13. The optical sensor module according to claim 1, wherein the sensor chip includes a plurality of internal conductive plugs penetrating through the chip body so as to electrically connect the active region to the substrate.

14. A sensor chip comprising a chip body having an active region located at a top side thereof and a recess portion depressed from a top surface thereof for accommodating a light-emitting component, wherein the recess portion has a depth greater than a thickness of the light-emitting component, the sensor chip further comprises a multi-functional structure disposed on an inner surface of the recess portion for connecting the light-emitting component to a substrate, the recess portion is spaced from all of side surfaces of the chip body, the multi-functional structure includes a redistribution layer, the redistribution layer includes a first conductive portion and a second conductive portion that are insulated from each other.

15. The sensor chip according to claim 14, wherein the multi-functional structure includes a shielding layer disposed on a sidewall surface of the recess portion and located between the light-emitting component and the active region for preventing the active region from receiving light emitted by the light-emitting component.

16. The sensor chip according to claim 14, wherein the multi-functional structure includes a conductive layer for electrically connecting the light-emitting component to the substrate.

17. The sensor chip according to claim 14, wherein the multi-functional structure includes a reflective layer disposed on a sidewall surface of the recess portion for reflecting light emitted by the light-emitting component.

18. The sensor chip according to claim 14, further comprising a protective material disposed in the recess portion for encapsulating the light-emitting component.

19. The sensor chip according to claim 14, further a plurality of internal conductive plugs penetrating through the chip body, one of the internal conductive plugs being electrically connected to the active region.

* * * * *